(12) United States Patent
Williams et al.

(10) Patent No.: US 8,919,348 B2
(45) Date of Patent: Dec. 30, 2014

(54) SYSTEM AND METHOD FOR MULTI-INSTRUMENT SURGICAL ACCESS

(75) Inventors: Michael S. Williams, Santa Rosa, CA (US); Richard S. Stack, Chapel Hill, NC (US); Geoffrey A. Orth, Sebastopol, CA (US); Jeffrey A. Smith, Petaluma, CA (US); Richard A. Glenn, Santa Rosa, CA (US); Daniel W. Fifer, Windsor, CA (US); William L. Athas, Chapel Hill, NC (US); Aurora Pryor, Durham, NC (US)

(73) Assignee: Transenterix Surgical, Inc., Morrisville, NC (US)

( * ) Notice: Subject to any disclaimer, the term of this patent is extended or adjusted under 35 U.S.C. 154(b) by 348 days.

(21) Appl. No.: 13/007,974

(22) Filed: Jan. 17, 2011

(65) Prior Publication Data

US 2011/0118545 A1 May 19, 2011

Related U.S. Application Data

(63) Continuation of application No. 11/804,063, filed on May 17, 2007, now Pat. No. 8,518,024, which is a (Continued)

(51) Int. Cl.
| | |
|---|---|
| A61B 17/00 | (2006.01) |
| A61B 1/018 | (2006.01) |
| A61B 1/00 | (2006.01) |
| A61B 17/29 | (2006.01) |
| A61B 17/34 | (2006.01) |
| A61B 17/02 | (2006.01) |
| A61B 19/00 | (2006.01) |

(52) U.S. Cl.
CPC ....... *A61B 1/018* (2013.01); *A61B 2017/00225* (2013.01); *A61B 1/00052* (2013.01); *A61B 1/00135* (2013.01); *A61B 17/0218* (2013.01); *A61B 17/29* (2013.01); *A61B 17/3403* (2013.01); *A61B 17/3421* (2013.01); *A61B 19/26* (2013.01); *A61B 2017/00278* (2013.01); *A61B 2017/003* (2013.01); *A61B 2017/2905* (2013.01); *A61B 2017/2906* (2013.01); *A61B 2017/3407* (2013.01); *A61B 2017/3445* (2013.01); *A61B 2017/3447* (2013.01); *A61B 2017/3486* (2013.01); *A61B 2019/5229* (2013.01); *A61B 1/00128* (2013.01)
USPC ........... 128/898; 606/139; 606/153; 606/205; 606/159; 606/194

(58) Field of Classification Search
USPC ........ 606/1, 139, 153, 205, 159, 194; 395/82, 395/83–96, 99; 600/102, 104, 109, 114, 600/117, 118, 217; 901/2, 3, 33, 34, 41, 44, 901/46; 128/898
See application file for complete search history.

(56) References Cited

U.S. PATENT DOCUMENTS

| | | | |
|---|---|---|---|
| 3,561,432 | A | 2/1971 | Yamaki et al. |
| 3,896,793 | A | 7/1975 | Mitsui |

(Continued)

FOREIGN PATENT DOCUMENTS

| | | | |
|---|---|---|---|
| EP | 1 586 275 | A3 | 12/2005 |
| JP | 54-136780 | | 10/1979 |

(Continued)

OTHER PUBLICATIONS

U.S. Appl. No. 60/813,030, Larkin, unpublished.

(Continued)

*Primary Examiner* — Aaron Roane

(57) ABSTRACT

A system for performing multi-tool minimally invasive medical procedures through a single instrument port into a body cavity includes a rigid tube carried by a mount. Cannulas having instrument channels and steerable distal ends extend distally from the rigid tube. During a procedure using the system, the mount is supported by an operating room fixture, and instruments are advanced through the steerable instrument channels. Manipulation of the instrument handles engages actuators positioned on the mount, which steer the distal ends of the cannulas through the action of pull cables. The distal ends of the instruments may thus be steered within the body by the distal ends of the steerable cannulas.

13 Claims, 22 Drawing Sheets

Related U.S. Application Data continuation-in-part of application No. 12/947,784, filed on Nov. 16, 2010, which is a continuation of application No. 11/789,381, filed on Apr. 24, 2007, now Pat. No. 7,833,156.

(60) Provisional application No. 60/801,113, filed on May 17, 2006, provisional application No. 60/801,034, filed on May 17, 2006, provisional application No. 60/819,235, filed on Jul. 7, 2006, provisional application No. 60/794,563, filed on Apr. 24, 2006.

(56) References Cited

U.S. PATENT DOCUMENTS

| | | |
|---|---|---|
| 3,915,157 A | 10/1975 | Mitsui |
| 4,112,932 A | 9/1978 | Chiulli |
| 4,146,019 A | 3/1979 | Bass et al. |
| 4,157,709 A | 6/1979 | Schuster et al. |
| 4,245,624 A | 1/1981 | Komiya |
| 4,407,273 A | 10/1983 | Ouchi |
| 4,436,087 A | 3/1984 | Ouchi |
| 4,686,965 A | 8/1987 | Bonnet et al. |
| 4,763,669 A | 8/1988 | Jaeger et al. |
| 4,841,949 A | 6/1989 | Shimizu et al. |
| 4,865,017 A | 9/1989 | Shinozuka |
| 5,025,778 A | 6/1991 | Silverstein et al. |
| 5,037,433 A | 8/1991 | Wilk et al. |
| 5,099,827 A | 3/1992 | Melzer et al. |
| 5,183,471 A | 2/1993 | Wilk |
| 5,217,453 A | 6/1993 | Wilk |
| 5,246,424 A | 9/1993 | Wilk |
| 5,269,772 A | 12/1993 | Wilk |
| 5,271,383 A | 12/1993 | Wilk |
| 5,273,026 A | 12/1993 | Wilk |
| 5,284,128 A | 2/1994 | Hart |
| 5,297,536 A | 3/1994 | Wilk |
| 5,312,391 A | 5/1994 | Wilk |
| 5,318,013 A | 6/1994 | Wilk |
| 5,336,227 A | 8/1994 | Nakao et al. |
| 5,347,989 A | 9/1994 | Monroe et al. |
| 5,353,783 A | 10/1994 | Nakao et al. |
| 5,368,015 A | 11/1994 | Wilk |
| 5,373,840 A | 12/1994 | Knighton |
| 5,386,818 A | 2/1995 | Schneebaum et al. |
| 5,391,156 A | 2/1995 | Hildwein et al. |
| 5,395,367 A | 3/1995 | Wilk |
| 5,400,770 A | 3/1995 | Nakao et al. |
| 5,405,344 A | 4/1995 | Williamson et al. |
| 5,417,697 A | 5/1995 | Wilk et al. |
| 5,423,830 A | 6/1995 | Schneebaum et al. |
| 5,441,507 A | 8/1995 | Wilk |
| 5,454,827 A | 10/1995 | Aust et al. |
| 5,458,131 A | 10/1995 | Wilk |
| 5,486,182 A | 1/1996 | Nakao et al. |
| 5,511,564 A | 4/1996 | Wilk |
| 5,520,678 A | 5/1996 | Heckele et al. |
| 5,601,588 A | 2/1997 | Tonomura et al. |
| 5,609,563 A | 3/1997 | Suzuki et al. |
| 5,624,380 A | 4/1997 | Takayama et al. |
| 5,645,519 A | 7/1997 | Lee et al. |
| 5,653,705 A | 8/1997 | de la Torre et al. |
| 5,702,408 A | 12/1997 | Wales et al. |
| 5,779,646 A | 7/1998 | Koblish et al. |
| 5,817,061 A | 10/1998 | Goodwin et al. |
| 5,876,325 A | 3/1999 | Mizuno et al. |
| 5,916,147 A | 6/1999 | Boury |
| 5,951,466 A | 9/1999 | Segermark et al. |
| 5,957,913 A | 9/1999 | de la Torre et al. |
| 6,033,426 A | 3/2000 | Kaji |
| 6,066,090 A | 5/2000 | Yoon |
| 6,085,749 A | 7/2000 | Wardle et al. |
| 6,099,506 A | 8/2000 | Macoviak et al. |
| 6,117,158 A | 9/2000 | Measamer et al. |
| 6,120,433 A | 9/2000 | Mizuno et al. |
| 6,159,200 A | 12/2000 | Verdura et al. |
| 6,168,607 B1 | 1/2001 | Wattiez et al. |
| 6,210,397 B1 | 4/2001 | Aboul-Hosn et al. |
| 6,217,555 B1 | 4/2001 | Hart et al. |
| 6,234,958 B1 | 5/2001 | Snoke et al. |
| 6,254,534 B1 | 7/2001 | Butler et al. |
| 6,315,770 B1 | 11/2001 | de la Torre et al. |
| 6,352,503 B1 | 3/2002 | Matsui et al. |
| 6,440,061 B1 | 8/2002 | Wenner et al. |
| 6,454,783 B1 | 9/2002 | Piskun |
| 6,458,074 B1 | 10/2002 | Matsui et al. |
| 6,468,203 B2 | 10/2002 | Belson |
| 6,488,620 B1 | 12/2002 | Segermark et al. |
| 6,527,753 B2 | 3/2003 | Sekine et al. |
| 6,569,105 B1 | 5/2003 | Kortenbach et al. |
| 6,582,364 B2 | 6/2003 | Butler et al. |
| 6,610,007 B2 | 8/2003 | Belson et al. |
| 6,669,674 B1 | 12/2003 | Macoviak et al. |
| 6,706,050 B1 | 3/2004 | Giannadakis |
| 6,783,491 B2 | 8/2004 | Saadat et al. |
| 6,800,056 B2 | 10/2004 | Tartaglia et al. |
| 6,811,532 B2 | 11/2004 | Ogura et al. |
| 6,837,846 B2 | 1/2005 | Jaffe et al. |
| 6,837,849 B2 | 1/2005 | Ogura et al. |
| 6,840,951 B2 | 1/2005 | de la Torre et al. |
| 6,846,287 B2 | 1/2005 | Bonadio et al. |
| 6,858,005 B2 | 2/2005 | Ohline et al. |
| 6,869,396 B2 | 3/2005 | Belson |
| 6,890,297 B2 | 5/2005 | Belson |
| 6,939,296 B2 | 9/2005 | Ewers et al. |
| 6,958,037 B2 | 10/2005 | Ewers et al. |
| 6,974,411 B2 | 12/2005 | Belson |
| 6,984,203 B2 | 1/2006 | Tartaglia et al. |
| 7,029,435 B2 | 4/2006 | Nakao |
| 7,052,454 B2 | 5/2006 | Taylor et al. |
| 7,081,089 B2 | 7/2006 | Bonadio et al. |
| 7,090,637 B2 | 8/2006 | Danitz et al. |
| 7,147,650 B2 | 12/2006 | Lee |
| 7,182,752 B2 | 2/2007 | Stubbs et al. |
| 7,285,112 B2 | 10/2007 | Stubbs et al. |
| 7,300,399 B2 | 11/2007 | Bonadio et al. |
| 7,316,699 B2 | 1/2008 | McFarlane |
| 7,338,473 B2 | 3/2008 | Campbell et al. |
| 7,338,513 B2 | 3/2008 | Lee et al. |
| 7,344,547 B2 | 3/2008 | Piskun et al. |
| 7,347,863 B2 | 3/2008 | Rothe et al. |
| 7,361,180 B2 | 4/2008 | Saadat et al. |
| 7,364,582 B2 | 4/2008 | Lee |
| 7,390,329 B2 | 6/2008 | Westra et al. |
| 7,410,483 B2 | 8/2008 | Danitz et al. |
| 7,491,165 B2 | 2/2009 | Kogasaka et al. |
| 7,615,066 B2 | 11/2009 | Danitz et al. |
| 7,637,905 B2 | 12/2009 | Saadat et al. |
| 7,833,156 B2 | 11/2010 | Williams et al. |
| 8,518,024 B2 | 8/2013 | Williams et al. |
| 2001/0049497 A1 | 12/2001 | Kalloo et al. |
| 2003/0045778 A1 | 3/2003 | Ohline et al. |
| 2003/0216619 A1 | 11/2003 | Scirica et al. |
| 2003/0233025 A1 | 12/2003 | Saadat et al. |
| 2003/0233026 A1 | 12/2003 | Saadat et al. |
| 2003/0233027 A1 | 12/2003 | Ewers et al. |
| 2003/0233056 A1 | 12/2003 | Saadat et al. |
| 2003/0233057 A1 | 12/2003 | Saadat et al. |
| 2003/0233058 A1 | 12/2003 | Ewers et al. |
| 2003/0233066 A1 | 12/2003 | Ewers et al. |
| 2003/0236505 A1 | 12/2003 | Bonadio et al. |
| 2004/0138525 A1 | 7/2004 | Saadat et al. |
| 2004/0138529 A1 | 7/2004 | Wiltshire et al. |
| 2004/0162568 A1 | 8/2004 | Saadat et al. |
| 2004/0186350 A1 | 9/2004 | Brenneman et al. |
| 2004/0249367 A1 | 12/2004 | Saadat et al. |
| 2005/0065397 A1 | 3/2005 | Saadat et al. |
| 2005/0065401 A1 | 3/2005 | Saadat et al. |
| 2005/0107663 A1 | 5/2005 | Saadat et al. |
| 2005/0107667 A1 | 5/2005 | Danitz et al. |
| 2005/0113640 A1 | 5/2005 | Saadat et al. |
| 2005/0137454 A1 | 6/2005 | Saadat et al. |
| 2005/0137455 A1 | 6/2005 | Saadat et al. |
| 2005/0137456 A1 | 6/2005 | Saadat et al. |

(56) References Cited

U.S. PATENT DOCUMENTS

| | | |
|---|---|---|
| 2005/0165272 A1 | 7/2005 | Okada et al. |
| 2005/0222495 A1 | 10/2005 | Okada et al. |
| 2005/0228224 A1 | 10/2005 | Okada et al. |
| 2005/0234294 A1 | 10/2005 | Saadat et al. |
| 2005/0234296 A1 | 10/2005 | Saadat et al. |
| 2005/0250990 A1 | 11/2005 | Le et al. |
| 2005/0251091 A1 | 11/2005 | Saadat et al. |
| 2005/0251176 A1 | 11/2005 | Swanstrom et al. |
| 2005/0251177 A1 | 11/2005 | Saadat et al. |
| 2005/0267335 A1 | 12/2005 | Okada et al. |
| 2005/0272977 A1 | 12/2005 | Saadat et al. |
| 2005/0273084 A1 | 12/2005 | Danitz et al. |
| 2005/0273085 A1 | 12/2005 | Danitz et al. |
| 2005/0277945 A1 | 12/2005 | Saadat et al. |
| 2005/0277975 A1 | 12/2005 | Saadat et al. |
| 2005/0288551 A1 | 12/2005 | Callister et al. |
| 2006/0020241 A1 | 1/2006 | Piskun et al. |
| 2006/0020287 A1 | 1/2006 | Lee et al. |
| 2006/0025652 A1 | 2/2006 | Vargas |
| 2006/0030755 A1 | 2/2006 | Ewers et al. |
| 2006/0036267 A1 | 2/2006 | Saadat et al. |
| 2006/0058582 A1 | 3/2006 | Maahs et al. |
| 2006/0111209 A1 | 5/2006 | Hinman et al. |
| 2006/0111210 A1 | 5/2006 | Hinman |
| 2006/0111615 A1 | 5/2006 | Danitz et al. |
| 2006/0111616 A1 | 5/2006 | Danitz |
| 2006/0161185 A1 | 7/2006 | Saadat et al. |
| 2006/0167416 A1 | 7/2006 | Mathis et al. |
| 2006/0178560 A1 | 8/2006 | Saadat et al. |
| 2006/0178562 A1 | 8/2006 | Saadat et al. |
| 2006/0183975 A1 | 8/2006 | Saadat et al. |
| 2006/0184161 A1 | 8/2006 | Maahs et al. |
| 2006/0189845 A1 | 8/2006 | Maahs et al. |
| 2006/0224174 A1 | 10/2006 | Smith et al. |
| 2006/0237022 A1 | 10/2006 | Chen et al. |
| 2006/0247500 A1 | 11/2006 | Voegele et al. |
| 2006/0258909 A1 | 11/2006 | Saadat et al. |
| 2007/0021737 A1 | 1/2007 | Lee |
| 2007/0049966 A1 | 3/2007 | Bonadio et al. |
| 2007/0093695 A1 | 4/2007 | Bonadio et al. |
| 2007/0123840 A1 | 5/2007 | Cox |
| 2007/0151390 A1 | 7/2007 | Blumenkranz |
| 2007/0167679 A1 | 7/2007 | Miyamoto et al. |
| 2007/0167680 A1 | 7/2007 | Miyamoto et al. |
| 2007/0221700 A1 | 9/2007 | Ortiz et al. |
| 2007/0221701 A1 | 9/2007 | Ortiz et al. |
| 2007/0225562 A1 | 9/2007 | Ortiz et al. |
| 2007/0255219 A1 | 11/2007 | Vaugh et al. |
| 2007/0276430 A1 | 11/2007 | Lee et al. |
| 2007/0283970 A1 | 12/2007 | Mohr et al. |
| 2007/0287884 A1 | 12/2007 | Schena et al. |
| 2007/0287889 A1 | 12/2007 | Mohr |
| 2007/0287992 A1 | 12/2007 | Diolaiti et al. |
| 2008/0027476 A1 | 1/2008 | Piskun |
| 2008/0045803 A1 | 2/2008 | Williams et al. |
| 2008/0051631 A1 | 2/2008 | Dejima et al. |
| 2008/0058595 A1 | 3/2008 | Snoke et al. |
| 2008/0064921 A1 | 3/2008 | Larkin et al. |
| 2008/0064927 A1 | 3/2008 | Larkin et al. |
| 2008/0064931 A1 | 3/2008 | Schena et al. |
| 2008/0065097 A1 | 3/2008 | Duval et al. |
| 2008/0065098 A1 | 3/2008 | Larkin |
| 2008/0065099 A1 | 3/2008 | Cooper et al. |
| 2008/0065100 A1 | 3/2008 | Larkin |
| 2008/0065101 A1 | 3/2008 | Larkin |
| 2008/0065102 A1 | 3/2008 | Cooper |
| 2008/0065103 A1 | 3/2008 | Cooper et al. |
| 2008/0065104 A1 | 3/2008 | Larkin et al. |
| 2008/0065105 A1 | 3/2008 | Larkin et al. |
| 2008/0065106 A1 | 3/2008 | Larkin |
| 2008/0065107 A1 | 3/2008 | Larkin et al. |
| 2008/0065108 A1 | 3/2008 | Diolaiti |
| 2008/0065109 A1 | 3/2008 | Larkin |
| 2008/0065110 A1 | 3/2008 | Duval et al. |
| 2008/0071288 A1 | 3/2008 | Larkin et al. |
| 2008/0071289 A1 | 3/2008 | Cooper et al. |
| 2008/0071290 A1 | 3/2008 | Larkin et al. |
| 2008/0071291 A1 | 3/2008 | Duval et al. |
| 2008/0086167 A1 | 4/2008 | Mastri et al. |
| 2008/0091170 A1 | 4/2008 | Vargas et al. |
| 2008/0183035 A1 | 7/2008 | Vakharia et al. |
| 2008/0188868 A1 | 8/2008 | Weitzner et al. |
| 2008/0188869 A1 | 8/2008 | Weitzner et al. |
| 2008/0188890 A1 | 8/2008 | Weitzner et al. |
| 2008/0221391 A1 | 9/2008 | Weitzner et al. |
| 2008/0243176 A1 | 10/2008 | Weitzner et al. |
| 2008/0255420 A1 | 10/2008 | Lee et al. |
| 2008/0255519 A1 | 10/2008 | Piskun et al. |
| 2008/0262294 A1 | 10/2008 | Ewers et al. |
| 2008/0262300 A1 | 10/2008 | Ewers et al. |
| 2008/0262525 A1 | 10/2008 | Chang et al. |
| 2008/0262539 A1 | 10/2008 | Ewers et al. |
| 2008/0275297 A1 | 11/2008 | Bakos et al. |
| 2008/0287862 A1 | 11/2008 | Weitzner et al. |
| 2009/0023985 A1 | 1/2009 | Ewers |
| 2009/0171161 A1 | 7/2009 | Ewers et al. |
| 2009/0227843 A1 | 9/2009 | Smith et al. |
| 2011/0060183 A1 | 3/2011 | Castro et al. |
| 2011/0066173 A1 | 3/2011 | Williams et al. |
| 2011/0112371 A1 | 5/2011 | Smith et al. |
| 2011/0184231 A1 | 7/2011 | Page et al. |

FOREIGN PATENT DOCUMENTS

| | | |
|---|---|---|
| JP | 5-184534 | 7/1993 |
| JP | 8117238 | 5/1996 |
| JP | 9-262239 | 10/1997 |
| WO | WO 96/04875 | 2/1996 |
| WO | WO 97/42889 A1 | 11/1997 |
| WO | WO 2005/009227 A1 | 2/2005 |
| WO | WO 2005/058239 A2 | 6/2005 |
| WO | WO 2006/019723 A2 | 2/2006 |
| WO | WO 2006/113216 A2 | 10/2006 |
| WO | WO 2007/146987 A2 | 12/2007 |

OTHER PUBLICATIONS

U.S. Appl. No. 60/813,126, Cooper, unpublished.
U.S. Appl. No. 60/813,028, Cooper, unpublished.
U.S. Appl. No. 60/813,129, Cooper, unpublished.
U.S. Appl. No. 60/813,173, Larkin, unpublished.
U.S. Appl. No. 60/813,131, Duval, unpublished.
U.S. Appl. No. 60/813,172, Cooper, unpublished.
U.S. Appl. No. 60/813,198, Larkin, unpublished.
U.S. Appl. No. 60/813,207, Diolaiti, unpublished.
U.S. Appl. No. 60/813,029, Larkin, unpublished.
U.S. Appl. No. 60/813,125, Larkin, unpublished.
U.S. Appl. No. 60/813,075, Larkin, unpublished.
In re PCT Patent Application No. PCT/US2007/011795, "International Preliminary Report on Patentability" and "Written Opinion of the International Searching Authority" 7 pages in lenth.
U.S. Appl. No. 60/813,328, Mohr, unpublished.

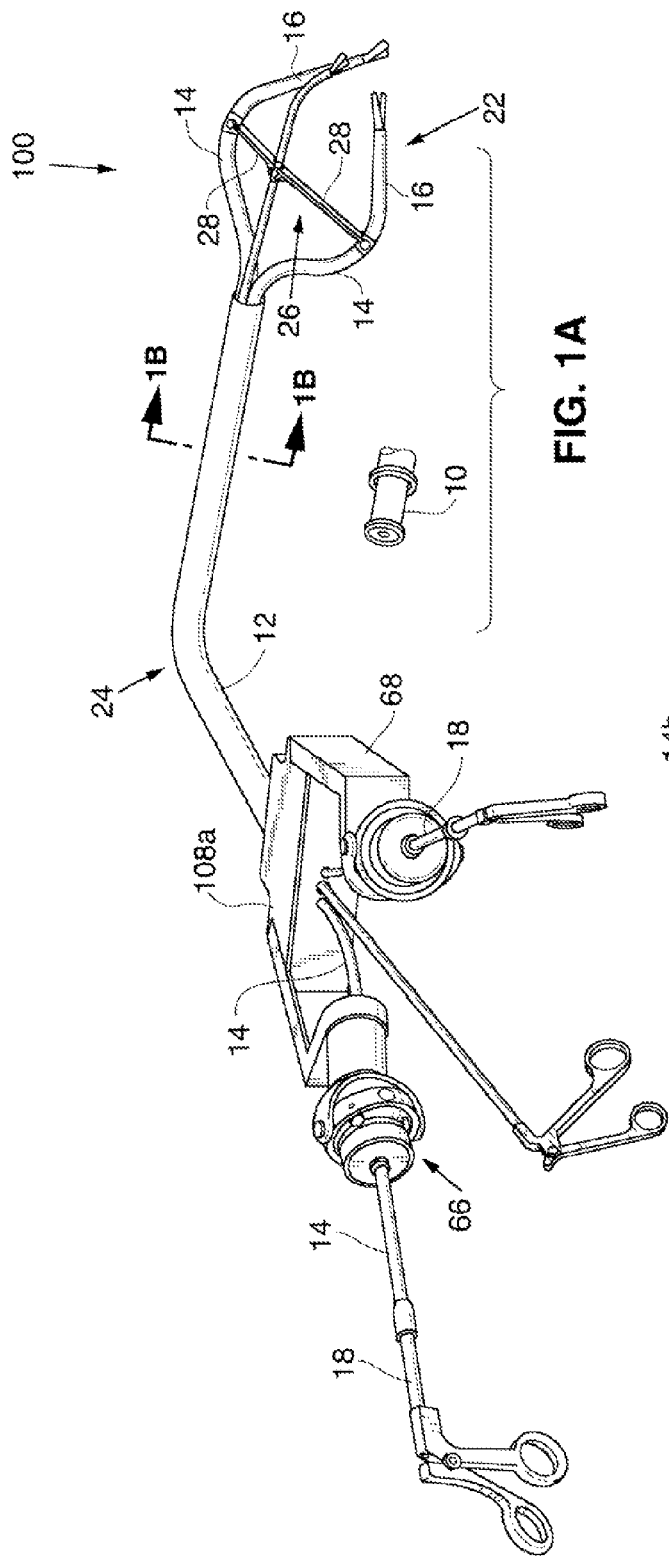
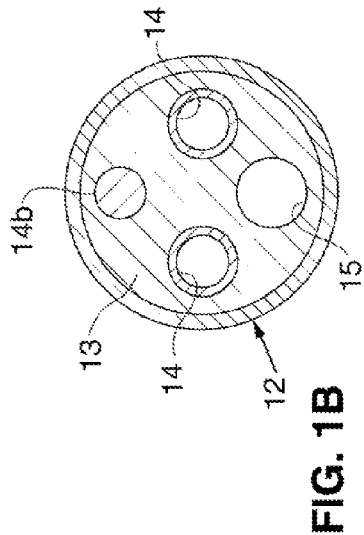
FIG. 1A
FIG. 1B

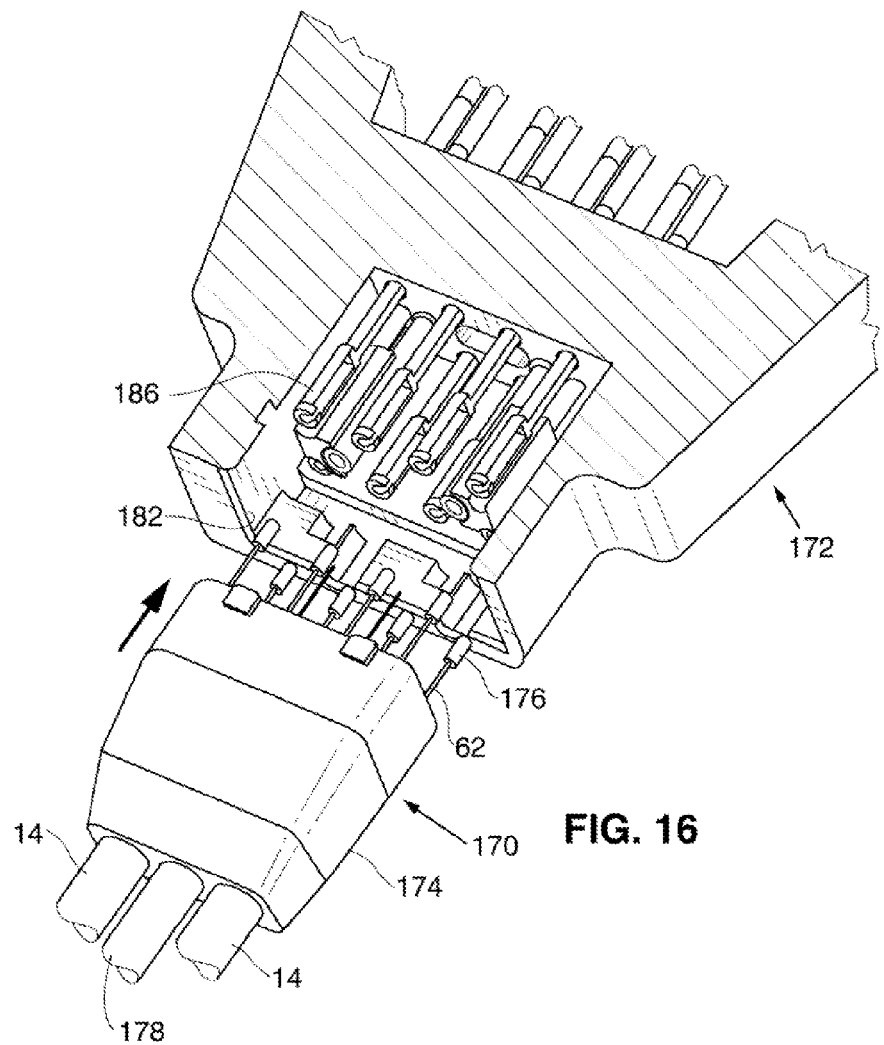
FIG. 16
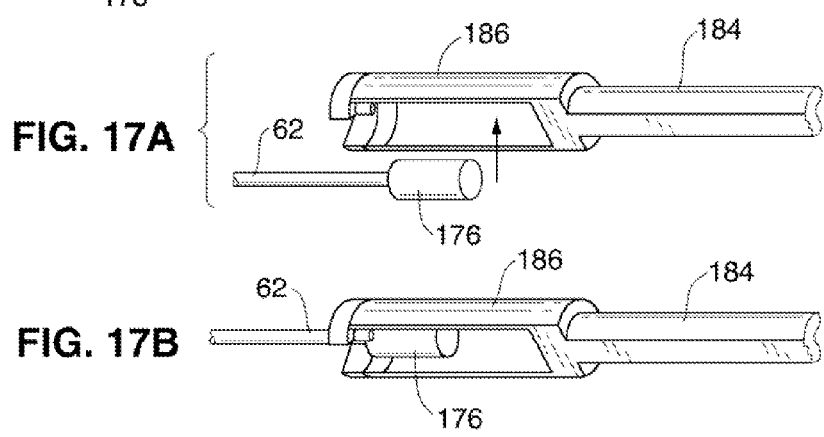
FIG. 17A
FIG. 17B

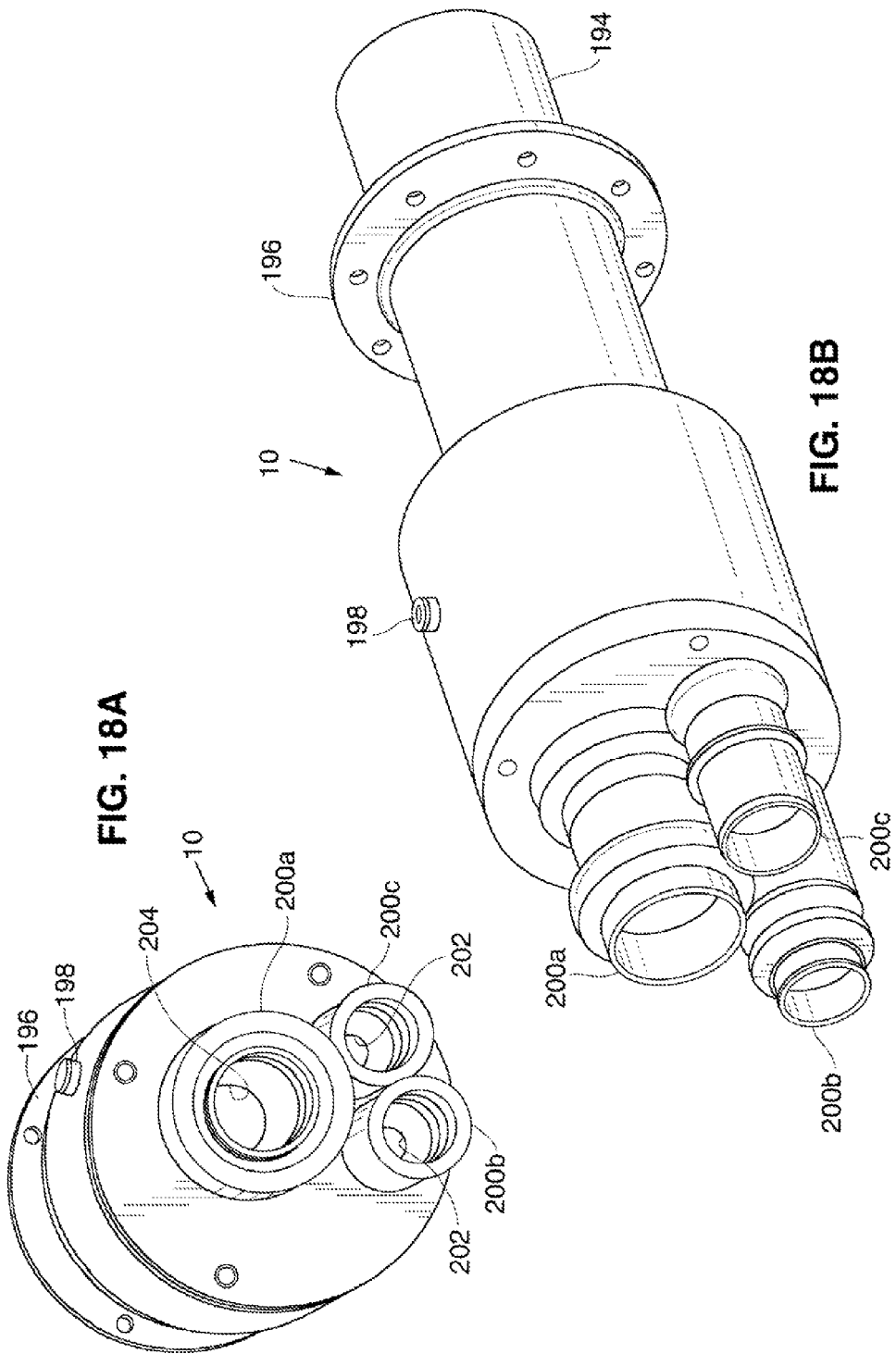

SYSTEM AND METHOD FOR MULTI-INSTRUMENT SURGICAL ACCESS

RELATED APPLICATIONS

This application is a continuation of U.S. application Ser. No. 11/804,063, now U.S. Pat. No. 8,518,024, filed May 17, 2007, which claims the benefit of U.S. Provisional Application Nos. 60/801,113, filed May 17, 2006, and 60/801,034, May 17, 2006, U.S. Provisional Application No. 60/819,235, filed Jul. 7, 2006. This application is also a Continuation-in-Part of U.S. application Ser. No. 12/947,784, filed Nov. 16, 2010, which is a continuation of U.S. Ser. No. 11/789,381, now U.S. Pat. No. 7,833,156, filed Apr. 24, 2007, which claims the benefit of U.S. Provisional Application No. 60/794,563, filed Apr. 24, 2006.

FIELD OF THE INVENTION

The present invention relates to the field of devices and procedures for use in performing surgery in the peritoneal cavity using access through a single port in the abdominal wall.

BACKGROUND OF THE INVENTION

Surgery in the abdominal cavity is typically performed using open surgical techniques or laparoscopic procedures. Each of these procedures requires incisions through the skin and underlying muscle and peritoneal tissue, and thus results in the potential for post-surgical scarring and/or hernias. Laparoscopic procedures, while less invasive than open surgical techniques, require multiple small incisions or ports to gain access to the peritoneal site using the various instruments and scopes needed to complete the procedure. The systems disclosed herein allow such procedures to be performed using only a single port.

BRIEF DESCRIPTION OF THE DRAWINGS

FIG. 1A is a perspective view showing a first embodiment of a single port surgical system.

FIG. 1B is cross-section view taken along the plane designated 1B-1B in FIG. 1A.

In FIG. 2C, the center retractor is shown in a downwardly deflected position, and phantom lines are shown to illustrate the retractor in an upwardly deflected position.

FIG. 16 is a detailed view of a portion of the system of FIG. 15 showing the socket and the hub. The socket is shown partially cut-away to permit viewing of features located inside it.

FIGS. 17A and 17B are perspective views of a pullwire head and control wire connector illustrating the step of coupling the two together.

FIGS. 18A and 18B are perspective views of one embodiment of an access cannula.

DETAILED DESCRIPTION OF THE DRAWINGS

Procedural Cannula and Support System

Figure 2A:
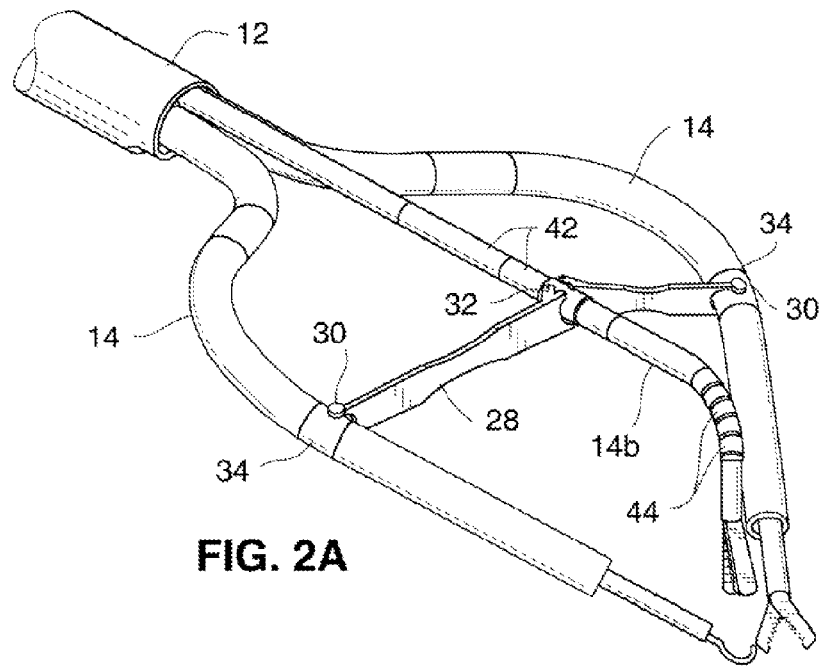
FIG. 2A is a top perspective view showing the distal portion of the single port surgical system of FIG. 1A.

The system illustrated in the accompanying drawings allows surgical procedures to be carried out through a single port formed in an abdominal wall. The port may be formed using conventional techniques in a chosen location, or it may be formed through the umbilicus.

For certain procedures, it would be advantageous to allow the surgeon to perform a single port surgical procedure in a manner that allows him/her to approach the surgical target within the peritoneal cavity from the same direction from which s/he would typically approach that same structure using a multi-port laparoscopic or open surgical procedure. For example, if a particular procedure utilizes an anterior approach to the treatment site when carried out using laparoscopic or surgical techniques, it would also be desirable to allow the surgeon to approach the treatment site from an anterior perspective even when using a single port technique. It is also desirable to orient the tools in a single port system so they will approach the operative tissue site in the abdominal cavity from the same direction from which those same tools would have approached the site if introduced through separate ports using known laparoscopic techniques. The system illustrated in the attached figures allows familiar laparoscopic approaches to be used using single port access, thus allowing a surgeon to easily and intuitively transition between single port surgical procedures and multi-port laparoscopic procedures.

Referring to FIG. 1, one embodiment of a single port surgical system 100 includes an instrument system 22 and a support system 24. In use, the support system 24 forms a sort of scaffold or chandelier within the body to support the instrument system 22 in a location that allows the surgeon to advance the instruments of the instrument system using a desired approach. Thus, for example, if performing a procedure that typically uses an anterior approach when carried out surgically or laparoscopically, the user might position the support system 24 adjacent the interior of the abdominal wall.

Support system 24 includes an elongate overtube 12 that is extendable through an opening in a body wall, and preferably through an access cannula 10 positioned in an incision or trocar puncture in the abdominal wall. The overtube 12 is a rigid or semi-rigid tubular cannula, although it may be deployable in a more flexible state and later converted to a self-supporting rigid state similar to the locking spine described in Applicants' co-pending U.S. application Ser. No. 11/789,381, Filed Apr. 24, 2007 which is incorporated by reference.

Referring again to FIG. 1A, instrument system 22 includes one or more procedural cannulas or tool cannulas 14 each having a lumen extending its length. Instruments 16 (e.g., forceps, endoscopes, suture devices, staplers) are extendable through the procedural cannulas 14 and into position at the target site in the peritoneal cavity, with the handles 18 of the instruments remaining outside the body. Two or three procedural cannulas are useful in that they allow for the simultaneous use of multiple instruments 16. In the FIG. 1A embodiment, a central retractor 14b is positioned between the tool cannulas 14. Retractor 14b has a handle 18b that can be manipulated to open/close the retractor jaws.

The procedural cannulas 14 and central retractor 14b extend through the overtube 12, allowing for a streamlined system that occupies a minimal amount of space. An endoscope 20 (FIG. 4B) can also extend through the overtube 12, allowing the user to observe the procedure being carried out at the distal end of the system. If needed, other instruments may extend directly through the overtube 12 towards the operative site and/or they may be supported by additional procedural cannulas.

If the system is to be used in procedures requiring insufflation, all or a portion of the length of the overtube may be filled with a plug formed of fill material 13 such as silicone or UV-curable polymer as shown in FIG. 1B. The fill material forms a seal around the procedural cannulas to prevent leakage of insufflation gas through the overtube. An additional endoscope lumen 15 may extend through the fill material for receiving an endoscope. The inner features of central retractor 14b are not shown in FIG. 1B.

Although the overtube 12 is described as formed of tubing, it can be replaced by any other structure that will bundle the tool cannulas and associated devices or cannulas (e.g. an endoscope or a cannula for the endoscope). As one example, instead of extending the tool cannulas etc. through an overtube, these devices may instead be bound together using shrink wrap or similar processes.

Figure 21:
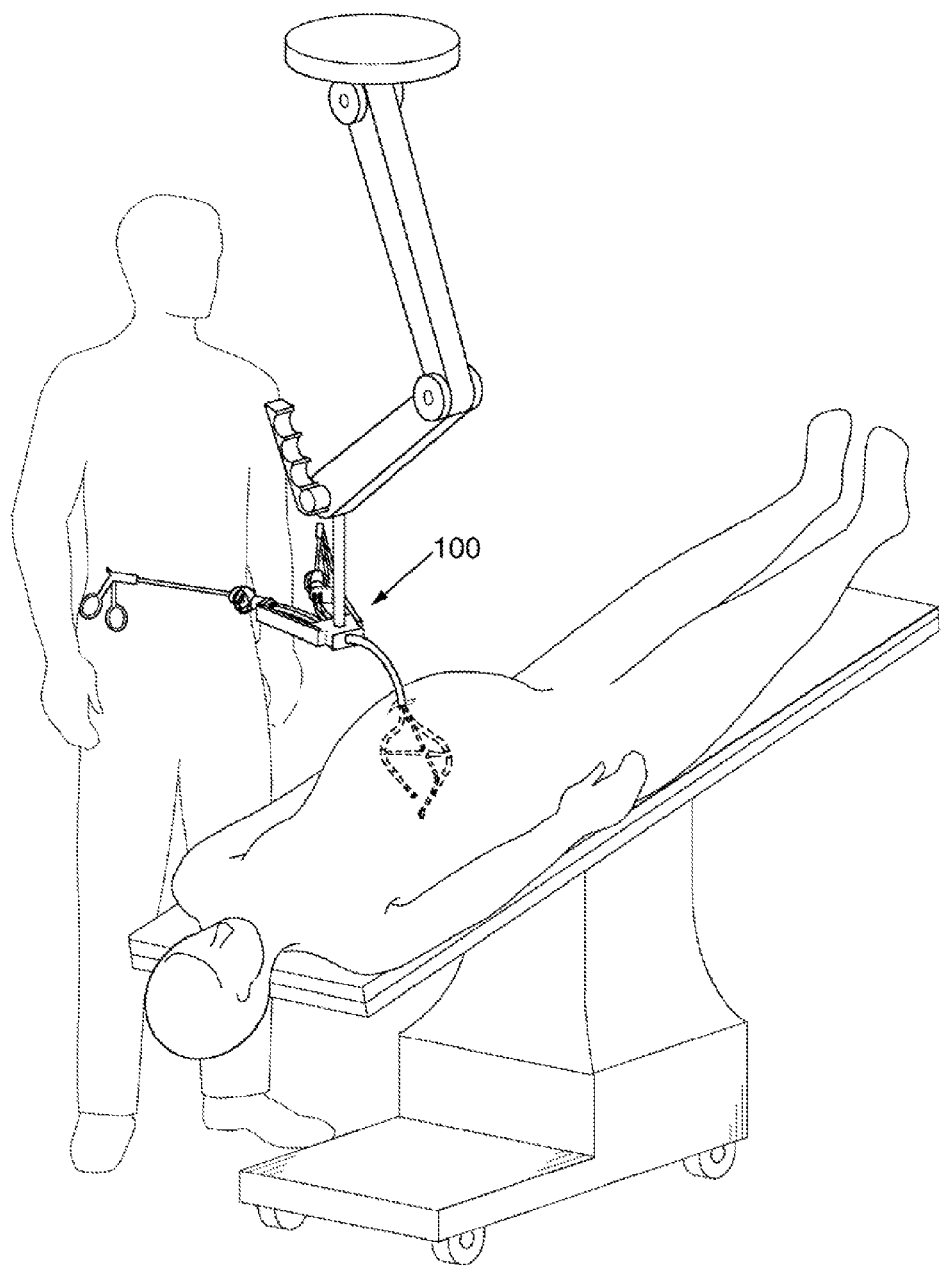
FIG. 21 schematically illustrates the single port surgical system of FIG. 1A coupled to a ceiling mount in a surgical theatre and having its distal end extending through an access cannula and into an insufflated abdominal cavity.

The system 100 includes features that support and orient the procedural cannulas 14 as appropriate for a given procedure. Referring to FIG. 1A, the tool cannulas are supported by a linkage system 26. In this embodiment, the linkage system 26 includes a pair of members 28. Each member 28 is attached by a corresponding one of the tool cannulas 14 by a first hinge 30 and to central retractor 14b (or, alternatively, to a longitudinal tool cannula like cannula 14a of FIG. 4A) by a second hinge 32. Hinges 30 may be mounted to corresponding collars 34 on the tool cannulas 14, and hinge 32 may be on a similar collar 36 (FIG. 2B) on retractor 14b. When linkage 26 is in the collapsed streamlined position, members 28 extend in a distal direction as shown in FIG. 21), with the tool cannulas 14 disposed near the longitudinal axis of the overtube for passage through the access cannula 10. To deploy the linkage 26, central retractor 14b is withdrawn proximally, causing the members 28 to pivot at hinges 30, 32.

Figure 2B:
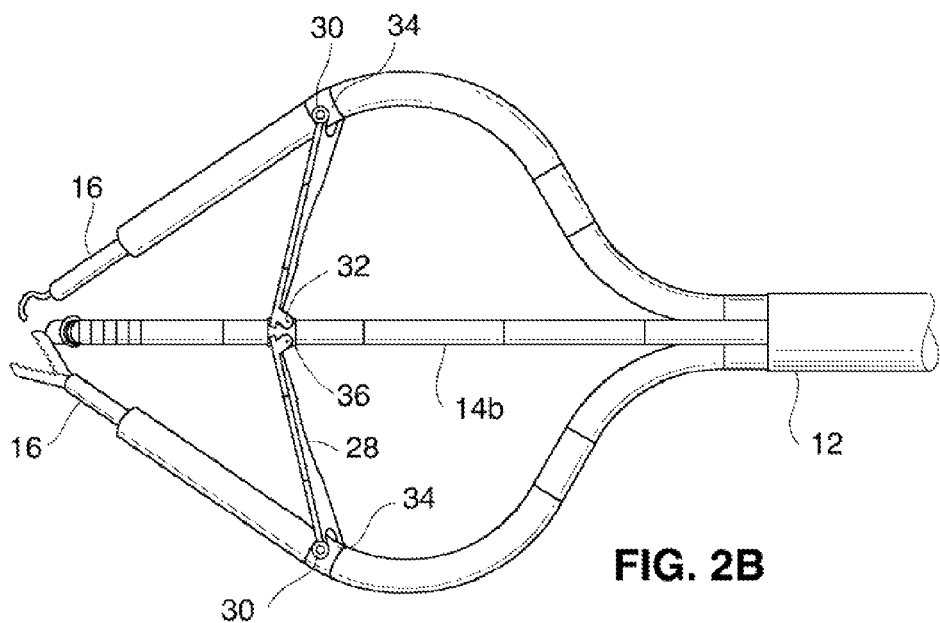
FIGS. 2B and 2C are a top plan view and a side elevation view of the linkage assembly of FIG. 2A.
Figure 2C:
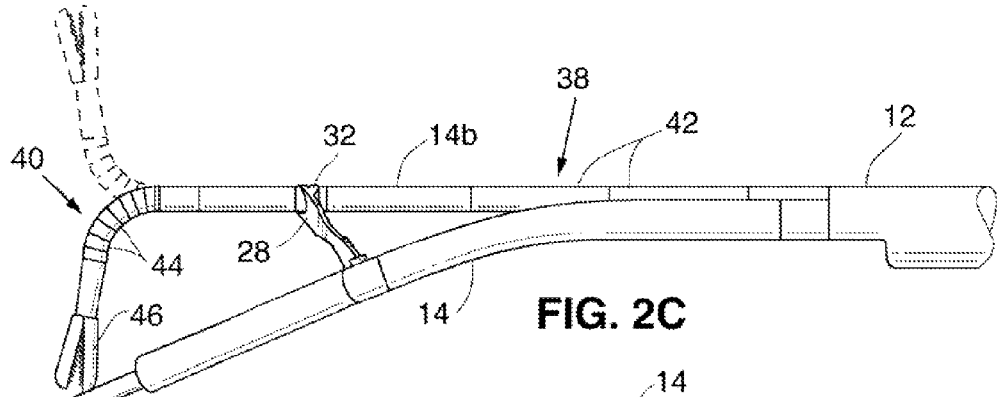

Referring to FIG. 2C, central retractor 14b includes a proximal section 38 and a distal section 40. Proximal section 38 is formed of a number of segments 42 strung onto one or more cables, with shorter segments 44 and an instrument tip 46 on the distal section 40. Cables within the retractor 14b are arranged such that the retractor becomes rigid when the cables are tensioned, and such that distal section 40 will deflect when the balance of tension within the cables is altered using controls (not shown) on the handle 18b or elsewhere outside the body. For example, retractor 14b may be deflectable towards and away from the body tissue as shown in FIG. 2C to allow tissue to be lifted by the retractor so the tissue may be acted upon by an instrument carried by one of the tool cannulas 14. Additional pull cables (not shown) are operable to open and close the jaws of the retractor tip 46.

Figure 2D:
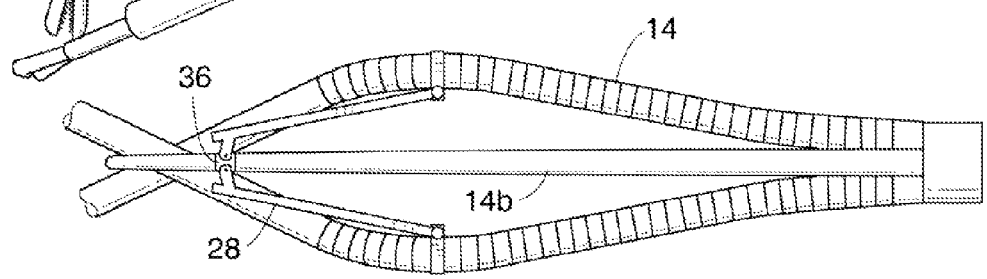
FIG. 2D is a top plan view of the linkage assembly of FIG. 2A in the streamlined position.

In the disclosed embodiments, each tool cannula 14 preferably has a pre-shaped curve in its distal region. The curve orients the cannula 14 such that when the linkage is opened, the instruments 16 (FIG. 1A) passed through the central lumens of the cannulas 14 can access a common treatment site. The preformed shape may be set using any of a number of methods. For example, cannulas 14 can be made of pre-curved tubing having rigidity sufficient to prevent buckling during use. Reinforcing braid made of stainless steel or other materials may be formed into the walls of the tubing in the rigid section of the cannulas 14. In other embodiments, the shaped region may have a segmented construction as shown in FIG. 2D (in which the linkage is in the collapsed position) and as similar to the segmented spine disclosed in co-pending U.S. application Ser. No. 11/789,381, Filed Apr. 24, 2007. With this design, individual spine segments are strung over one or more cables. The segments have individual shapes that collectively will give the tool cannulas the desired curvature (e.g. one that orients the cannulas as shown in FIG. 2A) when the cables running through the segments are tensioned. The entire length of the cannula may be segmented, or the distal portion may be formed of polymer tubing to allow flexibility.

Figure 3A:
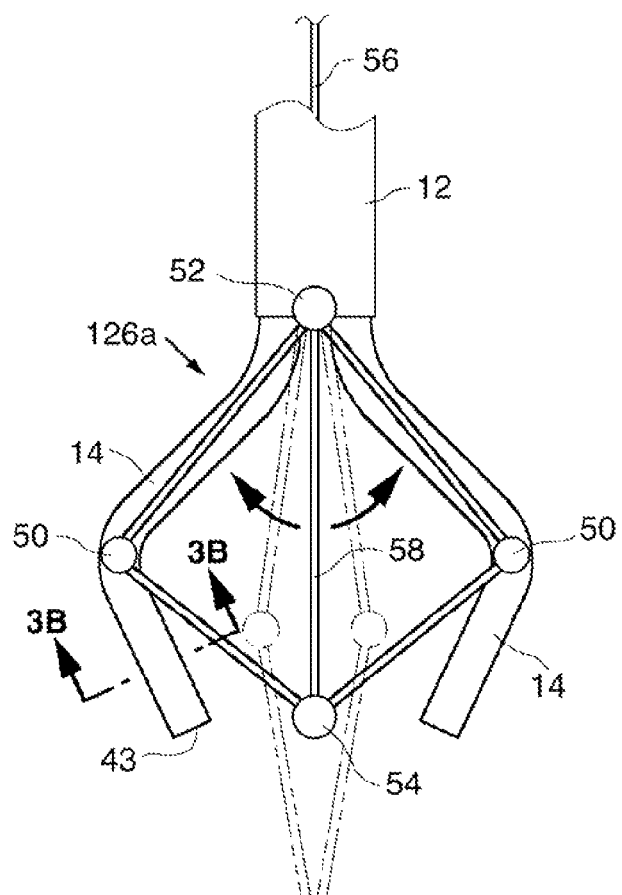
FIG. 3A is a perspective view showing the distal end of slightly modified single port surgical system using an alternative linkage configuration.

FIG. 3A is a perspective view of modified configuration for the distal end of the system 100, showing the distal ends of the tool cannulas 14. In this embodiment, a linkage 26a is pivotally connected to the cannulas 14 at pivot points 50 and couples the cannulas 14 to the overtube 12. Linkage 26a also provides structural support for the distal portions of the tool cannulas 14 and maintains the relative orientation of the cannulas 14. The linkage 26a is attached to a pivot mount 52 on the distal portion of the overtube 12. Another of the pivot mounts 54 is coupled to a pull wire 56 that extends proximally through overtube 12 to a location outside the body. In an alternative embodiment shown in FIGS. 4A and 4B, pivot mount 54 may be coupled to the distal portion of a third longitudinal tool cannula 14a extending longitudinally from the overtube 12, or to a similarly positioned tool shaft (e.g. shaft 14b, FIG. 2A). As another alternative, either or both of the pivot mounts 52, 54 may extend into free space as shown instead of being attached to the cannula 14a and/or overtube 12.

Dashed lines in FIG. 3A show the arrangement of the linkage 26a and pivot mounts 50 when that embodiments in the collapsed position. When in the streamlined position, the pivot mounts 50 are positioned side by side, thus orienting the tool cannulas 14 adjacent to one another. When in the deployed position, the pivot mounts are positioned approximately 3-7 inches apart, and more preferably approximately 4-6 inches apart. In other words, the lateral separation between the tool cannulas within the body (i.e. in a direction perpendicular to the longitudinal axis of the overtube 12) may be in the range of 3-7 inches.

Figure 4A:
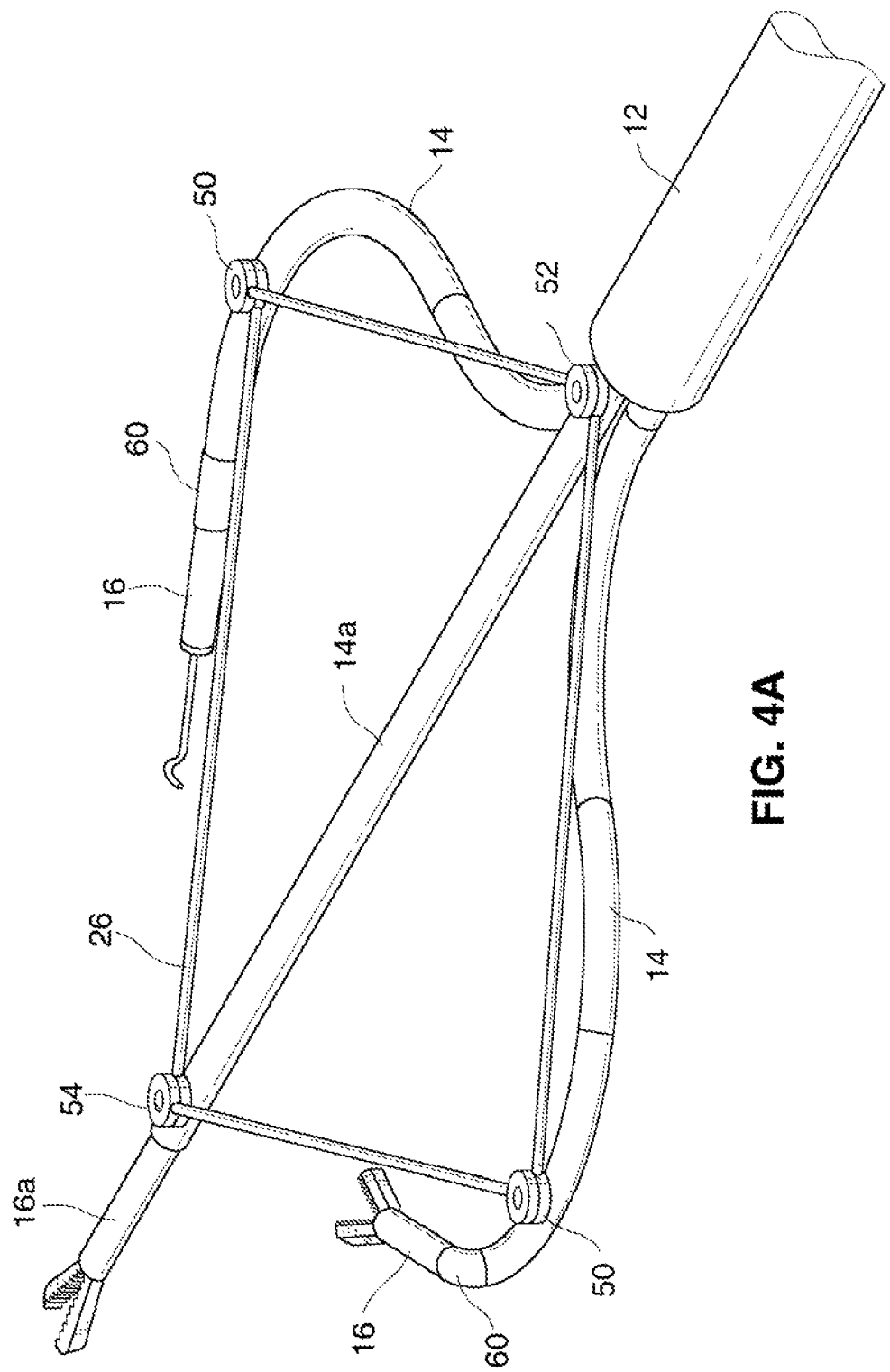
FIGS. 4A and 4B are a top perspective view and a bottom perspective view, respectively, of the distal end of another embodiment using an additional tool cannula.
Figure 4B:
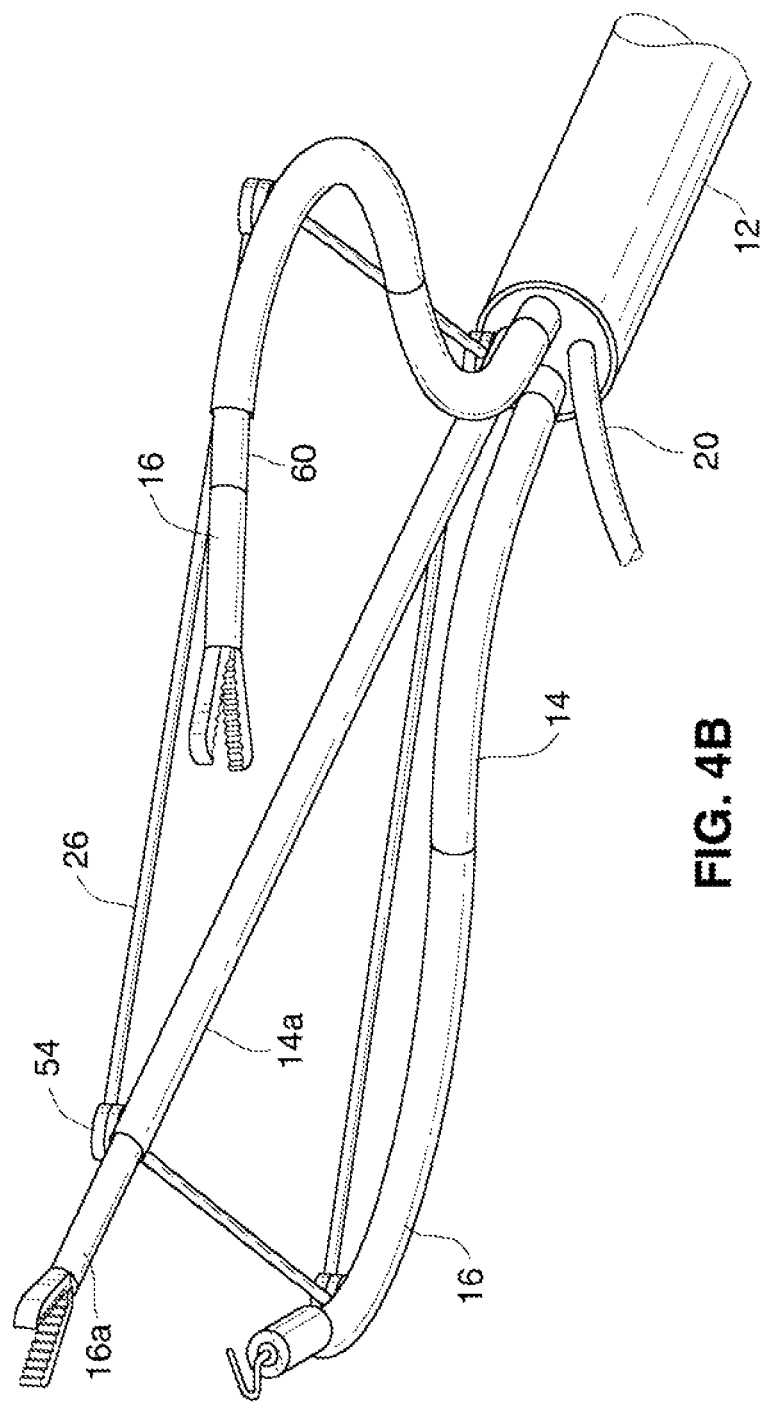

The linkage 26a of FIG. 3A may be deployed to the open position by withdrawing pullwire 56, whereas the FIG. 4A, 4B embodiment can be deployed by advancing the distal end of the longitudinal tool cannula 14c in a distal direction to move the linkage 26a out of the access cannula and/or to deploy the linkage to the expanded position. In other embodiments, one or more of the pivot points 50, 52, 54 may be spring loaded to facilitate expansion of the linkage 26a. Any combination of these deployment mechanisms, or others not specifically mentioned, may instead be used to deploy the linkage 26a in the peritoneal cavity.

Opening the linkage positions the cannulas 14 as shown in FIGS. 2A, 3A and 4A-4B and thus points the instruments 16 positioned in the cannulas 14 generally towards an operative tissue site. Once deployed within the body, a preferred system orients the tool cannulas 14 such that the tools 16 within the cannulas approach the tissue site from angles mimicking the angles of approach that those tool would have if introduced using a multiport laparoscopic procedure. This concept is discussed in greater detail in connection with FIG. 22.

The distal end of each tool cannula 14 has a region that is deflectable in multiple directions to allow positioning and manipulation of the operative ends of the instruments. This avoids the need fir sophisticated steerable surgical instruments. Instead, instruments 16 having flexible shafts are positioned in the tool cannulas 14, and steering of the instruments is achieved by deflecting the tool cannulas 14. Because the tools 16 are flexible, it may be necessary to "stiffen" the shaft of the tool 16 to allow the tool to be successfully used. A slideable stiffening cannula 60 (FIG. 4A) may be advanced from within the tool cannula 14 over a portion of the shaft of the tool 16 to effectively stiffen the tool's shaft during the procedure, thus allowing the tool to be pressed into contact with body tissue without buckling. Other internal structures such as stiffening mandrels, reinforcing collars or braids, may instead be used for this purpose. The segmented or "shape-lock" construction described above in connection with FIG. 2D may also be used for the tool cannulas to provide rigidity to the cannulas during tool usage.

Figure 2E:
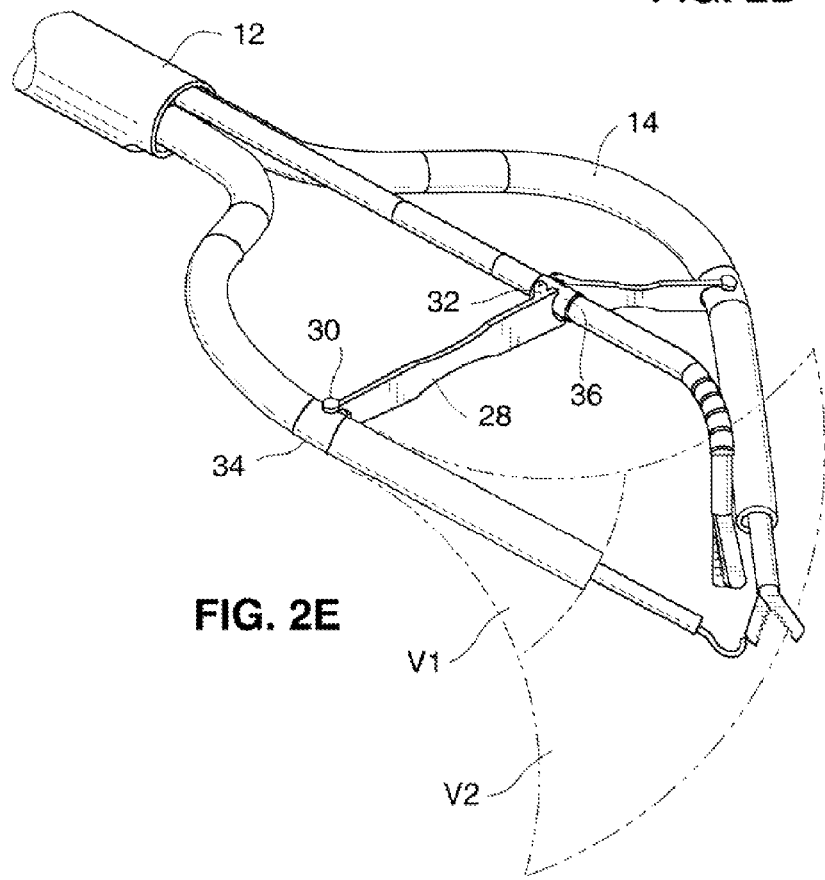
FIG. 2E is a perspective view similar to FIG. 2A illustrating exemplary movement patterns for the tool cannulas and associated tools.
Figure 3B:
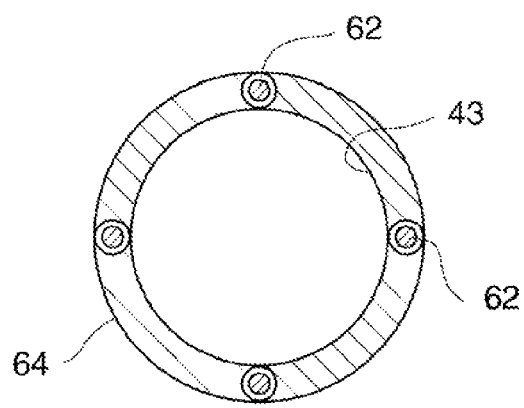
FIG. 3B is a cross-section view taken along the plane designated 3B-3B in FIG. 3A.

In a preferred embodiment, deflection of the tool cannulas 14 is performed using a pullwire system. Referring to FIG. 3B, pullwires 128 extend through corresponding pullwire lumens 64, preferably spaced at intervals of 90°. The distal ends of the pullwires are anchored in the distal sections of the cannula 14 such that the distal section of the cannula can be made to deflect in a desired direction by pulling on the desired combination of pullwires. FIG. 2E illustrates in dashed lines V1 a conical volumes defined by an exemplary movement pattern for the tool cannula 14, and the corresponding volume V2 defined by the tool 16 within the cannula 14.

Actuation of the pullwires is achieved using features that during use are positioned outside the body. A deflection system is provided that allows the user to intuitively actuate the pullwires for a particular one of the tool cannulas 14 by manipulating the handle 18 of the instrument 16 that resides within that tool cannula. For example, if the user wishes to have the distal end of a tool move in a downward direction, s/he will intuitively raise the handle 18 of that tool to cause the corresponding tool cannula to deflect downwardly, thus moving the tool to the desired position.

Referring to FIG. 1A, the proximal ends of the pullwires 62 extend from the proximal ends of the cannulas 14 and feed into a corresponding deflection system, which in the illustrated embodiments is a control gimbal 66.

Figure 14:
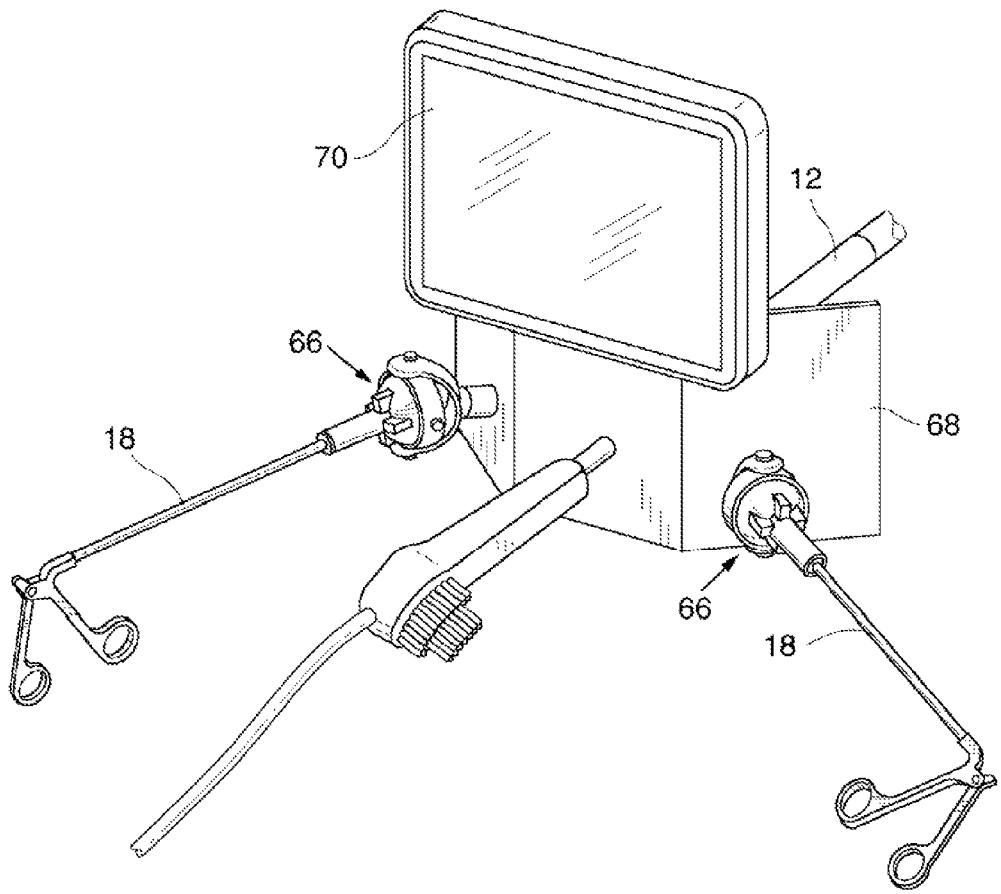
FIG. 14 is a perspective view of an alternative user interface for the system of FIG. 1A.
Figure 20:
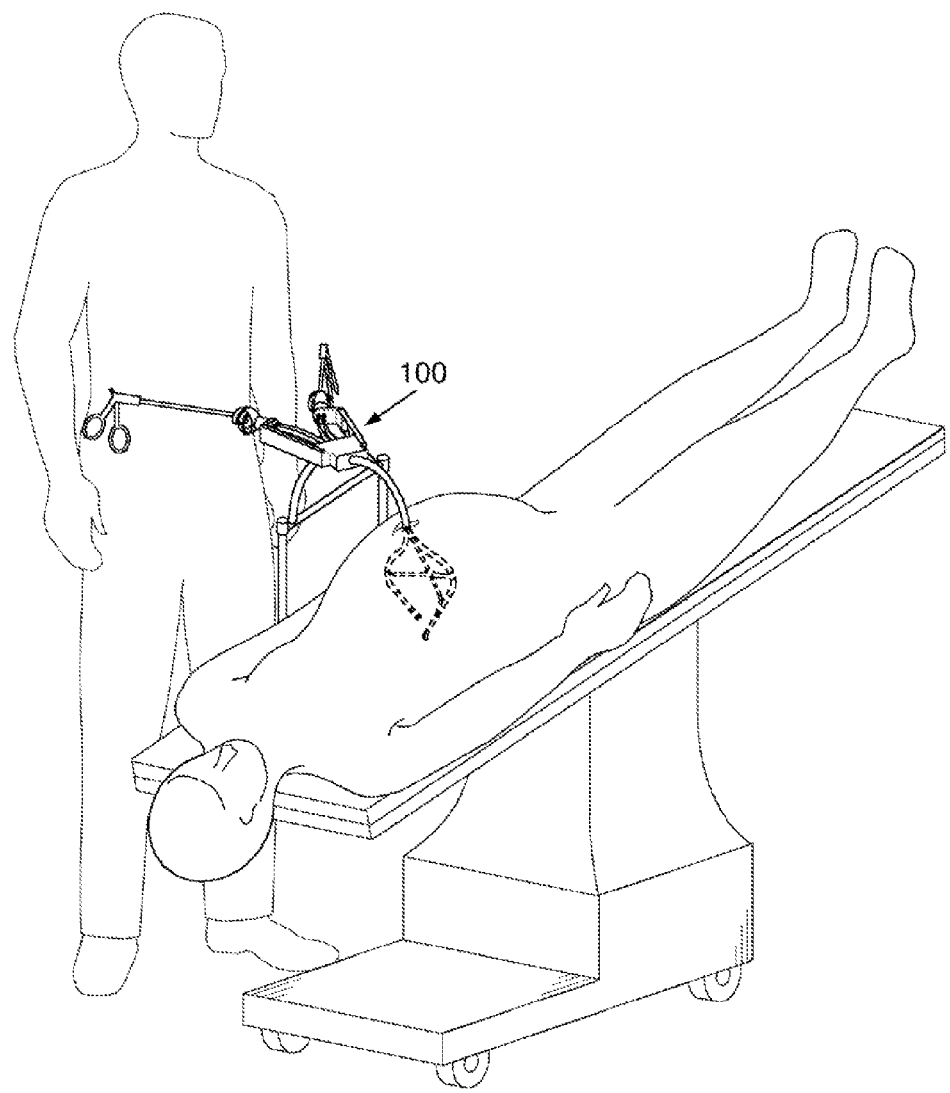
FIG. 20 schematically illustrates the single port surgical system of FIG. 1A coupled to a surgical table and having its distal end extending through an access cannula and into an insufflated abdominal cavity.

The gimbal 66 may be mounted to a work stand 68 as shown in FIG. 1A. In use the work stand 68 may be set on top of the patient's torso, mounted to a fixture within the operating room. The fixture might be one or both side-rails of the surgical table (FIG. 20), the ceiling of the surgical theatre (FIG. 21) or a cart positioned near the surgical table. In any case, the work stand 68 is positioned to give the surgeon convenient and intuitive access to the handles 18 while s/he observes the procedure on an endoscopic display (not shown). As shown in FIG. 14, use of the system may be facilitated by providing a "cockpit" for the user, coupling an endoscopic display 70 to a work stand 68 that supports the control gimbals 66, as well as the proximal controls for the endoscope 20, and optionally other ports for passing instruments through the access cannula to the peritoneal space.

The work stand 68 is proportioned to allow the surgeon to position his or herself in a comfortable position with his/her hands on the handles 18 of the tools 16. The work stand 68 preferably positions the tool handles 18 approximately 10-15 inches apart.

Figure 13:
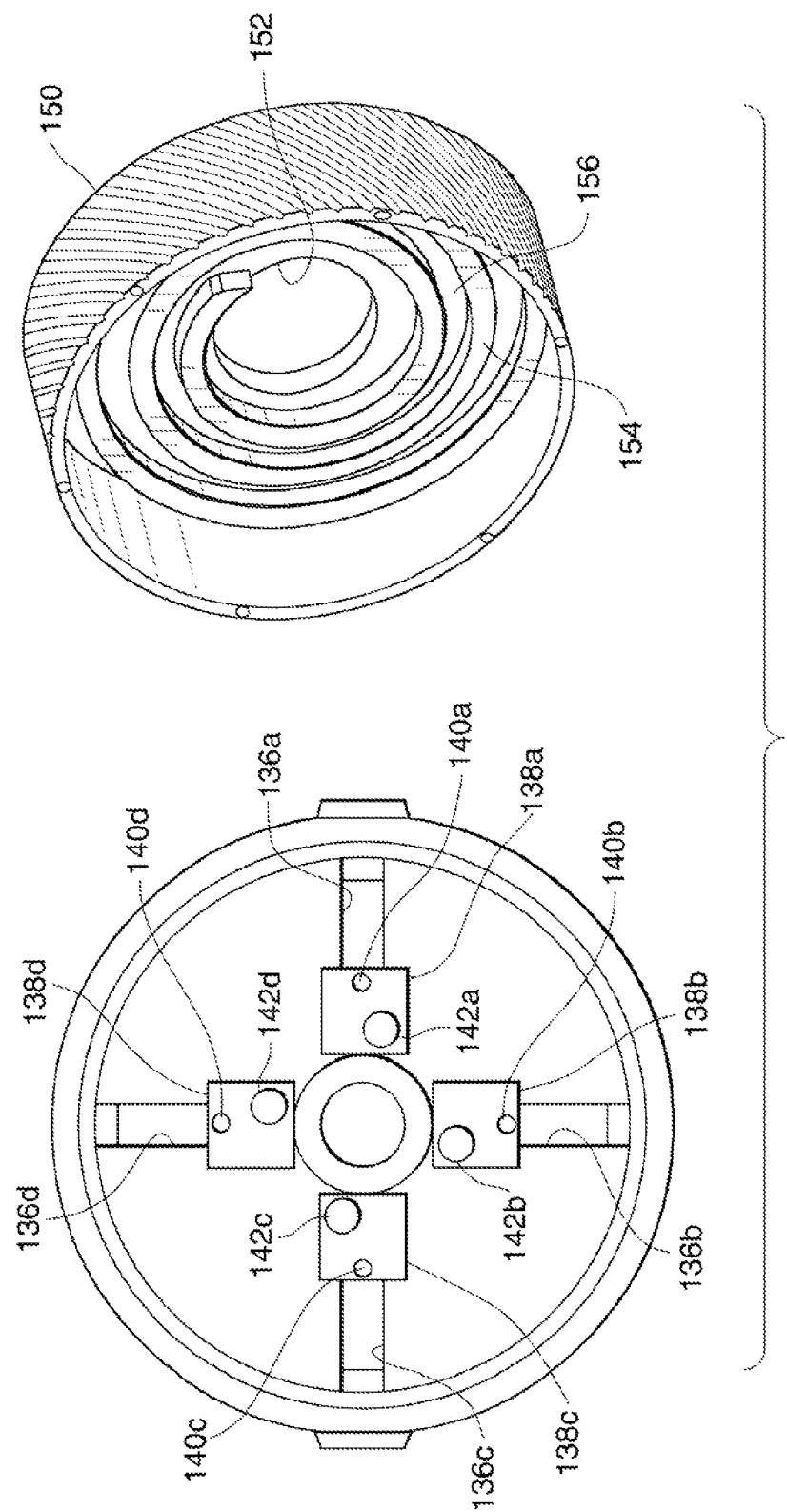
FIG. 13 is a plan view of the proximal surface of the ball of FIG. 12, with the cap removed and shown in perspective view.

A preferred control gimbal 66 is shown in FIG. 13. It includes a base 72 mounted to the work stand (not shown in FIG. 5) and having a tubular end piece having a channel 74. A c-shaped mount 76 is connected to the base 72 and includes a through hole 78 continuous with the channel of the tubular end piece 74. In a slight modification, the hole 78 might be accompanied by four separate through holes 78a-d might be used for receiving pull wires as in the FIG. 10 embodiment to be discussed below. A ring 80 is pivotally mounted to the mount 76 at pivot bearings 82. A semi-spherical ball 84 is pivotally mounted within the ring at pivots 86. Four pull-wire ports 88 extend from the interior of the ball 84 to its outer surface.

Instrument port 90 includes side channels 92 having distal openings 94 and proximal openings 96. The four pullwires 62 from the tool cannulas 14 extend through the tubular end piece 74 and each passes through hole 78, through the hollow interior of the ball 84, and out corresponding ones of the pull-wire ports 88 in the ball. The pullwires further extend into the instrument port side channels 92 and are secured there by anchors 98.

Instrument port 90 has a lumen 102 extending proximally from the spherical ball 84. The shaft 18 of an instrument 16 (see FIG. 12A, not shown in FIGS. 13-14) extends through the lumen 102 and the ball 84, through hole 78 in the c-shaped mount 76, and via tube 74 and the work stand 68 (FIG. 12A), into the corresponding tool cannula 14. The operative end of the instrument 16 extends from the distal end of the tool cannula 14.

When it becomes necessary for the surgeon to change the orientation of the distal end of an instrument 16, s/he need only intuitively move the handle 18 of that instrument and the distal portion of the instrument will deflect accordingly as a result of the action of the gimbal on the pullwires of the tool cannula. Vertical movement of the handle 18 will cause the ball 84 to rotate relative to pivots 86, thus applying tension to the upper or lower pullwire 62 to cause upward or downward deflection of the tool cannula 14 (and thus the distal end of the instrument 16). Lateral movement of the handle 18 will cause the ball 84 and ring 80 to rotate about pivots 82 and to therefore tension one of the side pullwires to change the lateral bend of the tool cannula 14. The control gimbal allows combinations of vertical and lateral deflection, giving 360° deflection as shown in FIG. 4E. Thus user may additionally advance/retract the tool 16 longitudinally within the tool cannula 14, and/or axially rotate the tool 16 relative to the tool cannula when required.

The control gimbal 66 includes a locking mechanism that allows an instrument orientation to be temporarily fixed until further deflection is needed. This feature allows a user to fix a trajectory for multiple instruments that are to be sequentially used at a particular location. For example, once the orientation of a tool cannula 14 is set, a certain step in the procedure may be performed using a first instrument passed through that cannula. When a subsequent step requiring a different instrument is to be performed, the instruments are exchanged without moving the tool cannula 14. This allows the second instrument to be advanced to the exact location at which it is needed without additional steering.

Figure 7A:
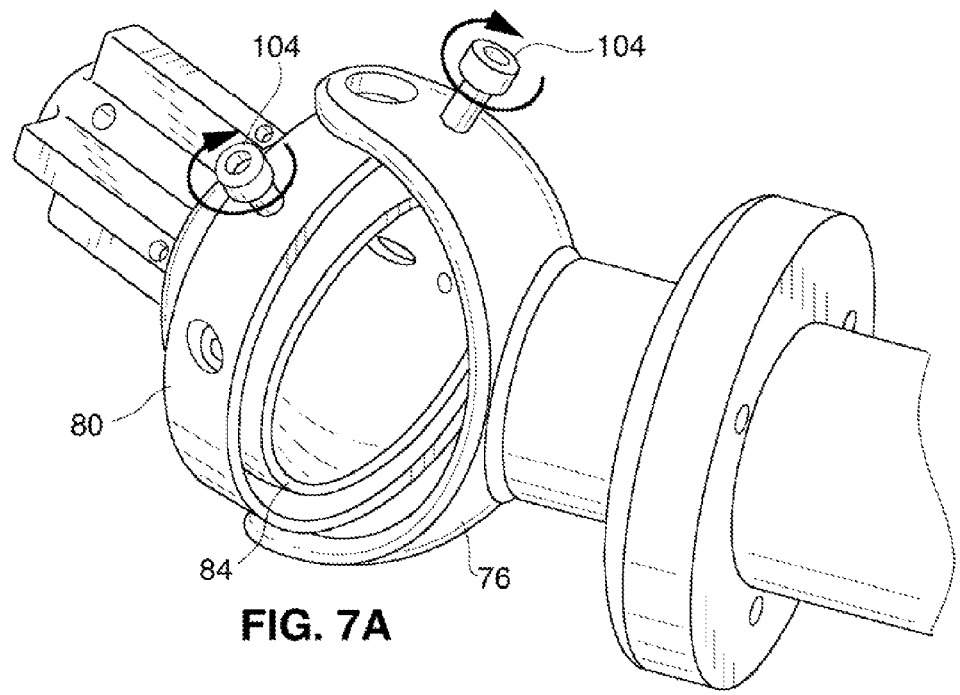
FIGS. 7A and 7B are perspective views of the gimbal assembly of FIG. 5 showing two exemplary locking mechanisms.
Figure 7B:
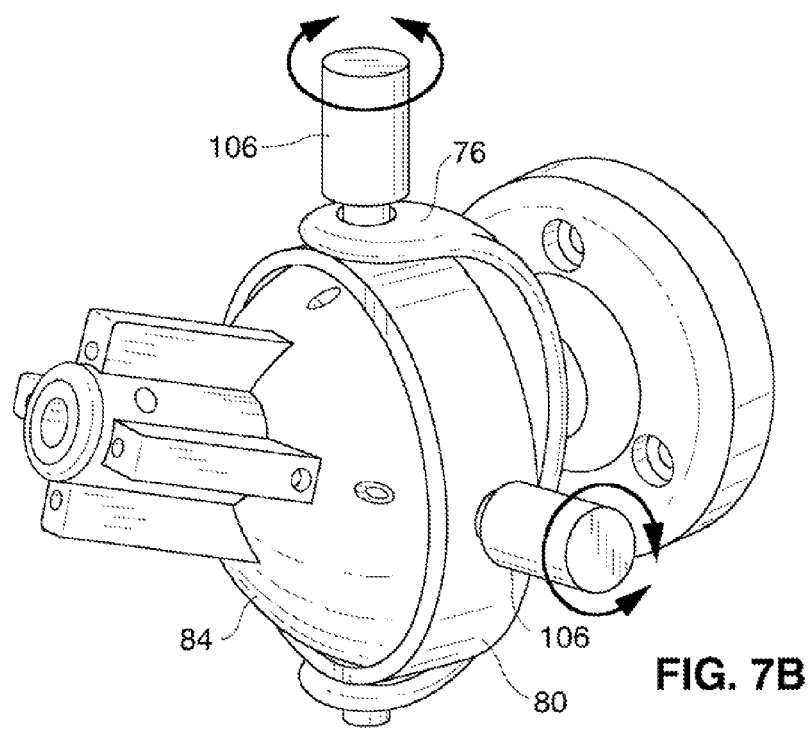

One exemplary locking mechanism includes a pair of locking screws 104 that are tightened as shown by arrows in FIG. 7A to lock the C-mount 76 to the ring 80 and to lock the ring 80 and the ball 84. Alternatively, as shown in FIG. 7B, a simple pneumatic shaft lock 106 could be employed on each of the gimbals' pivot axes. A solenoid or similar device might be used in place of the pneumatic lock 106.

Figure 8A:
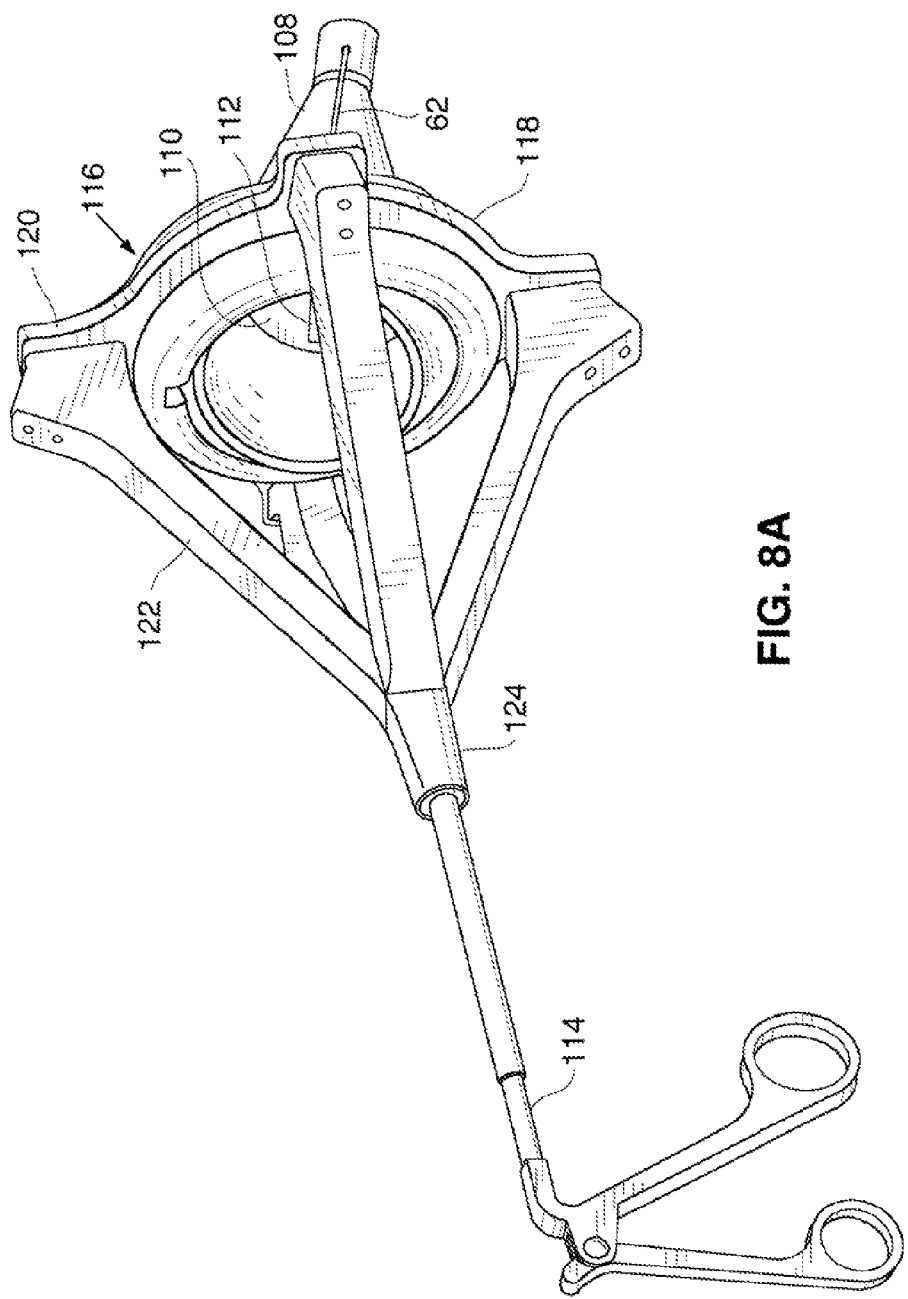
FIGS. 8A and 8B are perspective views of an alternative gimbal system.
Figure 8B:
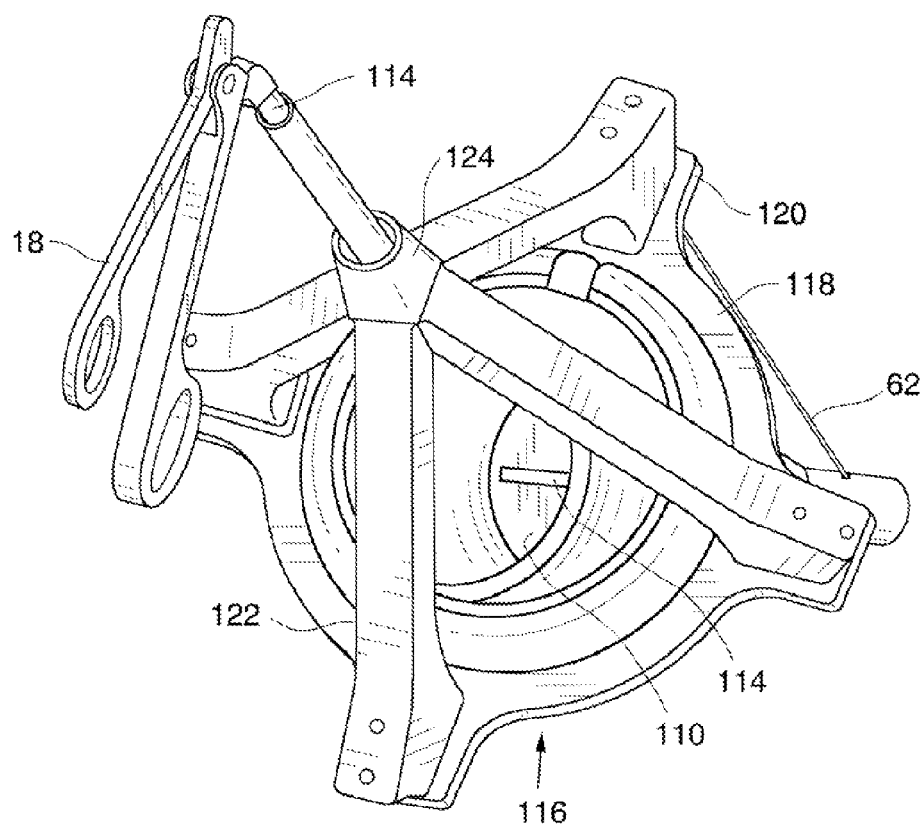

An alternate gimbal arrangement is shown in FIGS. 8A and 8B. As shown, a cone shaped instrument port 108 is mounted to the proximal end of each cannula, and includes a diaphragm seal 110 having a slit 112 sealable around an instrument shaft 114 passed into the instrument port 108. In FIGS. 16A and 16B only the handle of instrument shaft 114 is shown to permit easier viewing of the surrounding features.

A gimbal 116 includes a collar 118 mounted on the instrument port 108 and four wings 120 radiating from the collar 118. Each pullwire 62 is coupled to one of the wings 120. Struts 122 extend proximally from the wings 120 and are joined to a sleeve 124 through which a portion of the instrument shaft 114 extends. Collar 118 is moveable relative to the instrument port 108, and in particular collar 118 is rotatable about its central axis, and pivotable in multiple directions. Movement of the collar 118 places one or more of the pullwires 62 under tension and results in deflection of the cannula 14. Since the instrument shaft 114 is coupled to the collar 118 by struts 122, a user can manipulate the instrument shaft 114 handle in an intuitive manner similar to a joystick to allow the user to steer the distal end of the cannula 14 in the desired direction.

Figure 9:
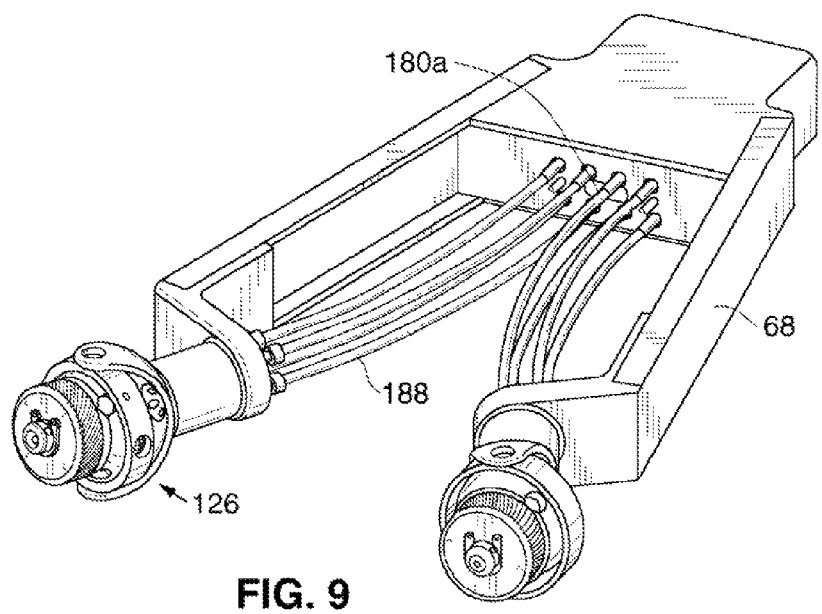
FIG. 9 is a detailed perspective view of the proximal end of a procedural cannula and support system using yet another alternative gimbal system.
Figure 10:
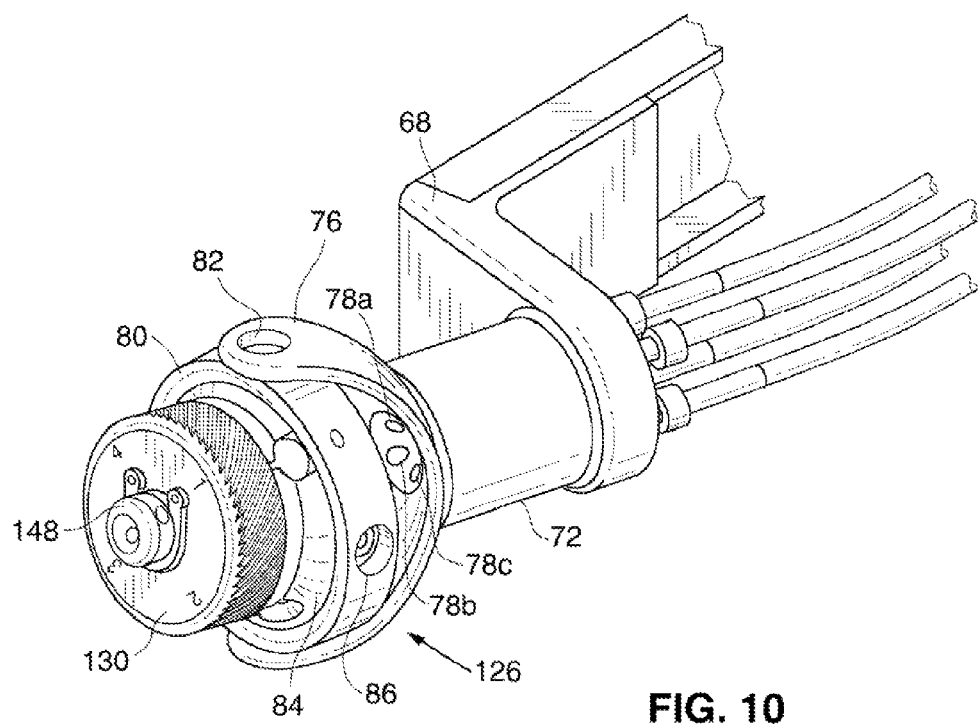
FIG. 10 shows the gimbal system of the FIG. 9 embodiment.

FIGS. 9-10 illustrate a gimbal system similar to that described in connection with FIG. 5, but that is modified to allow a user to adjust the sensitivity of the gimbals. In other words, the gimbal can be fine tuned such that the amount of deflection of the tool cannulas corresponds directly to the amount by which the user moves the tool handles 18 within the gimbal system, or the amount of deflection can be greater than or less than the corresponding movement of the tool handles.

Figure 5:
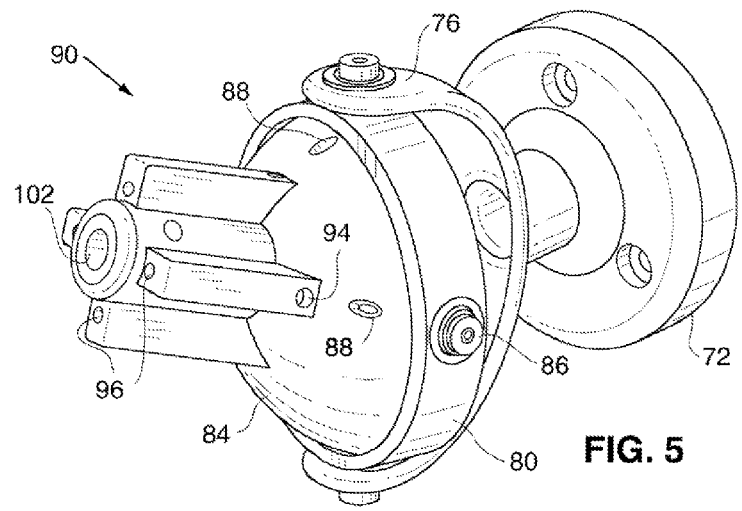
FIGS. 5 and 6 are a perspective view and a cross-sectional side view of a gimbal assembly.
Figure 6:
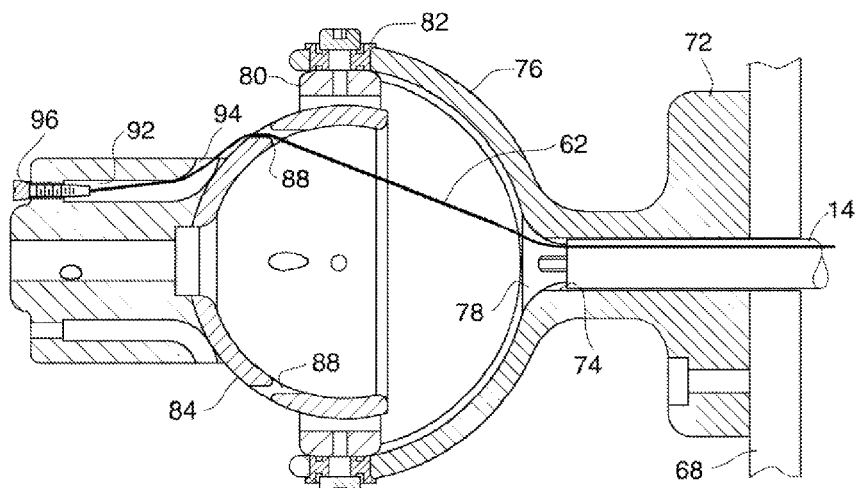

Referring to FIG. 10, many of the features of the gimbal 126 are similar to those of gimbal 66 of FIGS. 5 and 6. These similar features include base 72, which is coupled to work stand or frame 68. Four through-holes 78a-d (three of which are visible in FIG. 10), one for each pull wire, extend from c-shaped mount 76 through base 72. The pullwires feed into the through-holes 78a-d from cable housings 128 that pass through the frame 68. The more distal segments of the pullwires extend from the frame 68 into the tool cannulas 14 extending distally from the frame 68.

A ring 80 is pivotally mounted to mount 76 at pivots 82, and semi-spherical ball 84 is pivotally mounted within the ring 80 at pivots 86.

The gimbal 126 of FIG. 10 differs from the gimbal 66 of FIGS. 5-6 in its use of a microadjustment assembly 130. As with the prior gimbal arrangements, the four pullwires of one of the tool cannulas terminate in the gimbal at 90 degree quadrants. Motion of the instrument shaft 18 (FIG. 1A) alters the tension on the various pullwires, which causes deflection of the tool cannula tip and corresponding movement of the tool within the tool cannula. The effect lever arm of each pull wire is altered in the FIG. 19 embodiment by moving the point of termination of each pull wire towards or away from the gimbals' center of rotation. Moving the pullwire terminations away from the center of rotation causes movement of the tool cannula 14 to be amplified relative to the movement of the tool handle 18, whereas moving the pullwire terminations towards the center of rotation decreases the amplification.

Figure 11:
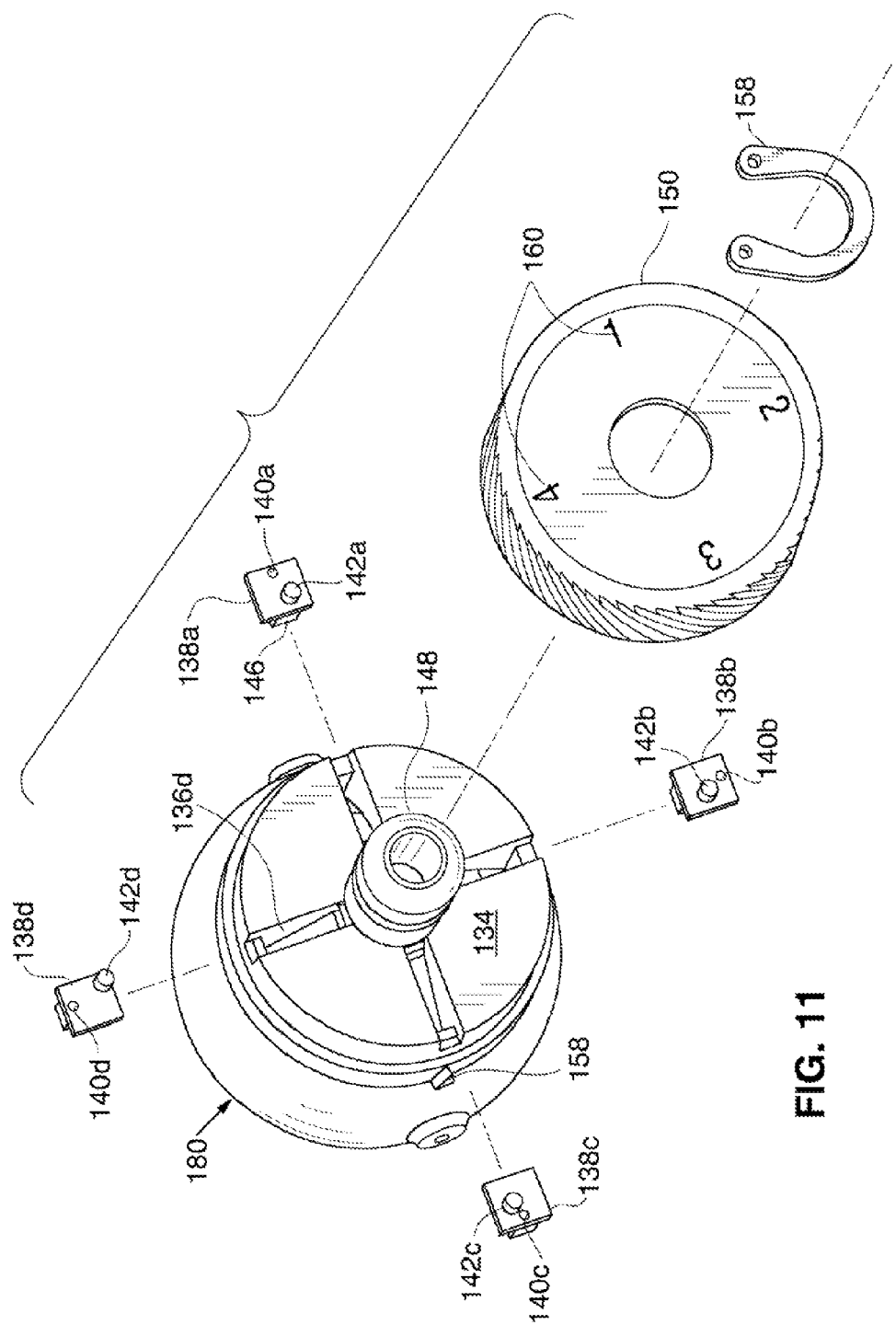
FIG. 11 is an exploded view of the gimbal system of FIG. 19.
Figure 12:
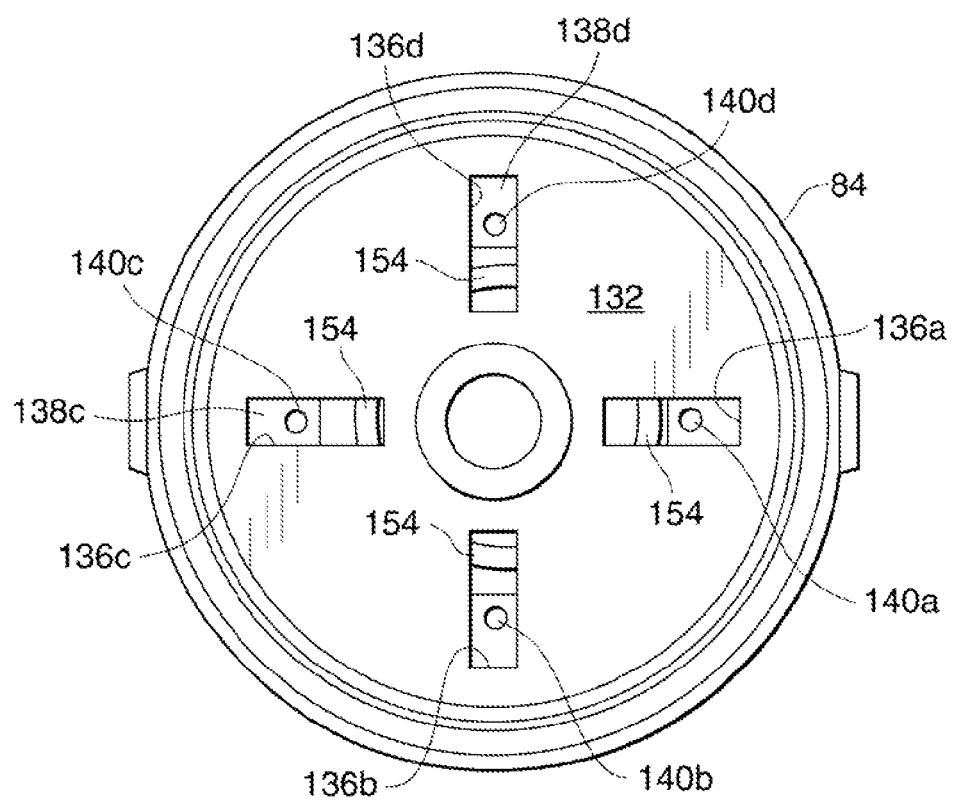
FIG. 12 is a plan view of the distal surface of the ball of the gimbal system of FIG. 10.

Ball 84 includes a distal surface 132 as shown in FIG. 12, and a planar proximal surface 134 as shown in FIG. 11. Four radial slots 136a-d extend through between the surfaces 132, 134. Referring to FIG. 11, four sliding terminal plates 138a-d, each including a pullwire terminal 140a-d and a proximally-extending follower pin 142a-d, are positioned in contact with the planar proximal surface 134. A peg 146 on the distal side of each terminal plate is received in the corresponding one of the slots 136a-d.

Each pullwire used to deflect the tool cannula extends through one of the slots 136a-d and is anchored within a terminal 140a-d of one of the four sliding terminals 138a-d. FIG. 12 shows the distal facing side 132 of the ball 84, with the terminals 140a-d positioned over the slots 136a-d. The pull wires themselves are not shown.

A tubular instrument port 148 is centrally positioned on the proximal surface 134 of the ball 84. A retainer cap 150 covers the surface 134, such that the instrument port 148 extends through a central opening 152 in the retainer cap. The sliding terminal plates 138a-d are sandwiched between the surface 134 and the retainer cap 150. FIG. 13 shows the cap 150 removed from the ball 84. The inner, distal facing, surface of the cap 150 includes a spiral rib 154 defining a spiral shaped slot 156. Each of the follower pins 142a-d of the terminal plates 138a-d is disposed within the spiral slot 156.

A retaining ring 158 is engaged with the instrument port 148 and functions to hold the cap 150, terminal plates 138a-d, and ball 84 together such that the follower pins 142a-d remain within the spiral slot 156. Cap is rotatable in clockwise and counterclockwise directions relative to the instrument port 148. Rotation of the cap will increase or decrease the sensitivity of the gimbal system. More specifically, if the cap is rotated in a first direction, the spiral rib 154 will cause the pins 142a-d to advance through the spiral slot towards the outer circumference of the cap, causing the terminal plates to slide radially outwardly within slots, thereby increasing the sensitivity of the gimbal system. If the cap is rotated in a second direction, the pins will advance through the spiral slot toward the center of the cap, causing the terminal plates to slide radially inwardly within the slots so as to loosen the tension on the pullwires and to decrease the sensitivity of the gimbal system. Markings 160 on the cap 150 and a corresponding pointer 158 instruct the user as to the level of sensitivity achieved when the cap is in one of the designated rotational positions relative to the pointer 158.

In alternative configurations for adjusting gimbal sensitivity, the user may have the option to set different sensitivity levels for different ones of the pull wires.

The system is preferably packed in a kit containing instructions for use instructing the user to use the system in the manner disclosed herein.

Figure 15:
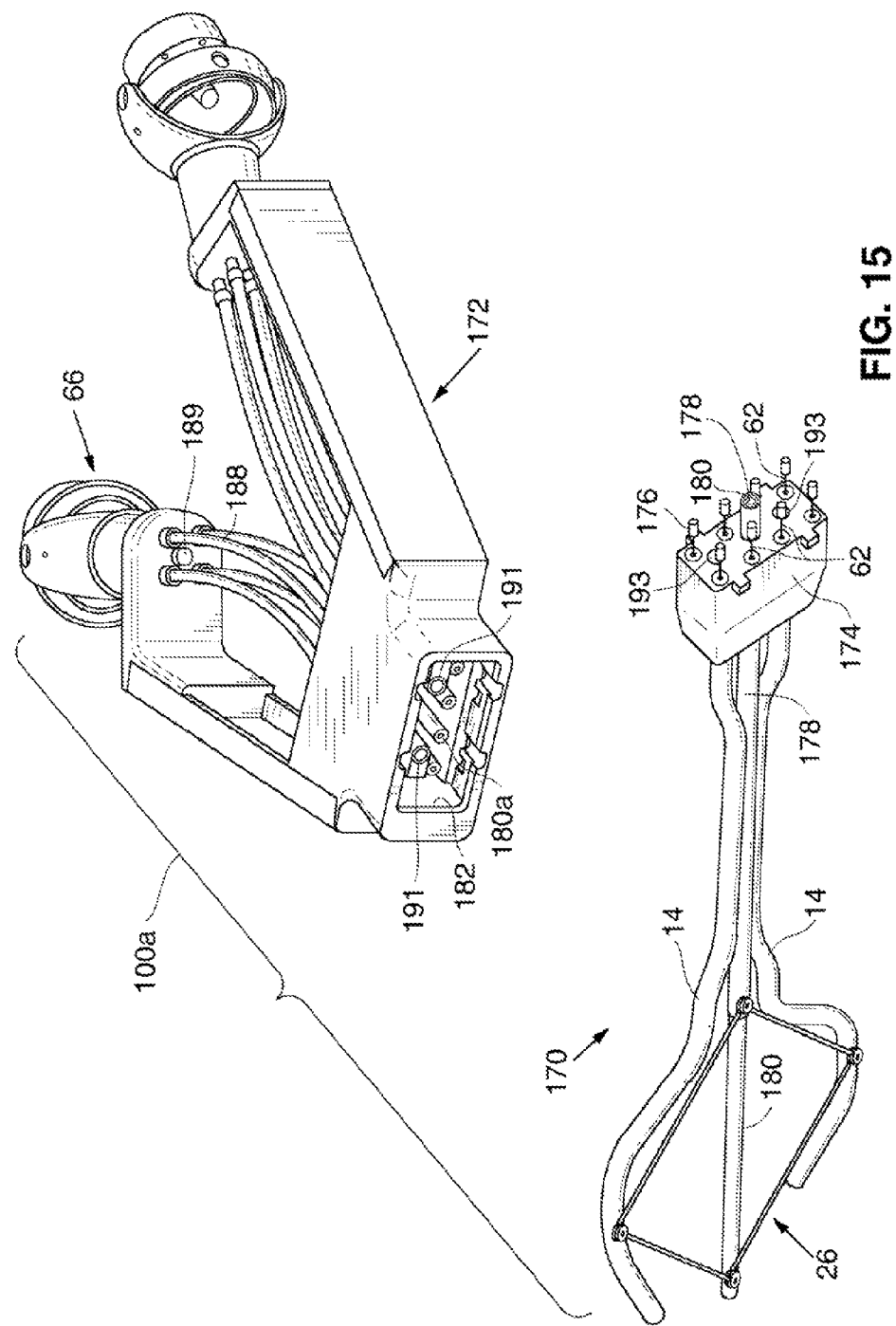
FIG. 15 is a perspective view showing an alternate single port surgical system having a detachable proximal component. The proximal and distal components are show separated from one another.

FIG. 15 shows a modified system 100A which differs from the system of FIG. 1A in that it includes a distal section 170 that is detachable from the proximal section 172 for disposal or sterilization. On the distal section 170, tool cannulas 14 extend from a hub 174, with each of the pullwires 62 from the tool cannulas 14 extending through the hub and terminating proximally of the huh as shown. Each pullwire 62 includes a head 176 or crimp on its proximal end as shown. In the FIG. 15 embodiment, a central tool cannula 178 also extends through the hub and is coupled to pivot mount 52 of the linkage 26. An additional cannula 180 (or alternatively, a tool) is coupled to the pivot mount 54 and is longitudinally moveable to deploy or collapse the linkage in a manner similar to that described in connection with FIGS. 4A and 4B.

The proximal section 172 includes a socket 182 for receiving the hub 174. A plurality of control wires 184 are positioned with their distal ends within the socket. Each control wire 184 includes a connector 186 at its distal end. Each control wire 184 extends through the frame and through a control wire tube 188. The distal end of each control wire 184 is coupled to the gimbal 126 in the same manner in which the pull wires are shown to be connected to the gimbals of FIGS. 5-8B. A central port 180a (see also FIG. 9) extends through the mount 68 and allows passage of an endoscope or other tool into tool cannula 180.

During assembly of the proximal and distal sections 172, 170, the control wires 184 are coupled to corresponding ones of the tool cannula pull wires 62, so that manipulation of tool handles 18 (FIG. 1A) within the gimbals 126 will deflect the tool cannulas 14 in the same manner as described above. To connect the control wires 184 and pull wires 62, the head 176 of each pull wire 62 is inserted into and engaged with the connector 186 of a control wire 184 as illustrated in FIGS. 17A and 17B. The hub 174 is seated within the socket 182 to securely connect the proximal and distal sections 172, 170.

As with the previously described embodiments, the shafts of instruments extend through instrument ports in the gimbals. See instrument 148 in the FIG. 10 embodiment. Referring again to FIG. 15, each the tool shaft (not shown but see shaft 17 in FIG. 1A) extends through an opening 189 in the portion of mount that supports the gimbal, and extends approximately in parallel to the control wire tubes 188. The shaft further extends out a port 191 positioned in socket 182 and into a corresponding port 193 in the hub 174

FIGS. 18A and 18B give one example of a rigid access cannula 10 which includes a distal end 194 insertable into an incision formed in a body wall. The incision may be an incision or trocar puncture formed through the abdominal wall or other body wall, or through the umbilicus. The access cannula 10 may be unsupported by additional hardware, or it might include a mount that couples to a side-rail of the surgical table so as to support and stabilize the access cannula 10 throughout the procedure.

A flange 196 surrounds the external surface of the cannula 10 and is positioned to make contact with the skin surrounding the incision. A side port 198 is positioned to receive insufflation gas from an appropriate source. Insufflation gas introduced via port 198 will inflate the abdominal cavity to enlarge the working space available for the procedure. Inflation of the abdominal cavity will cause a seal to form between the flange 196 and the tissue surrounding the incision. If necessary, a substance or material (e.g. silicone, rubber, adhesive, gel, etc.) may be positioned between the flange and the tissue to facilitate sealing.

One or more flexible (e.g. rubber) fittings 200a-c extend from the proximal end of the access cannula 10. Each fitting gives access to the interior of the access cannula 10. The individual fittings 200a-c may lead to separate lumens or to a single common lumen within the access cannula. In a preferred embodiment, a single lumen having an inner diameter of 15-35 mm is used. During use of the system, instruments to be passed into the body are inserted through the fittings into the access cannula. As shown in FIG. 18B, seals 202 (e.g., silicone, rubber, or other suitable material) are positioned to seal against the outer surfaces of instruments such as the overtube 12 and any other instruments passed through them. Sealing is desirable to prevent loss of insufflation pressure during the procedure. Each seal has a central opening 204 that preferably has an inner diameter that is smaller than the outer diameter of the instrument or collection of instruments to be passed through it. The access cannula 10 preferably includes an internal seal that prevents loss of insufflation pressure during times when any or all of the fittings 200a-c is without an instrument. For example, if each fitting is associated with a separate lumen, duck bill valves may be positioned within each lumen to form a seal when no instrument is present in that lumen. If only a single lumen is used, a single duck bill valve may be used. Stoppers may also be positioned in the fittings when needed.

In one embodiment the access cannula 10 is approximately 6 inches in length.

Figure 19A:
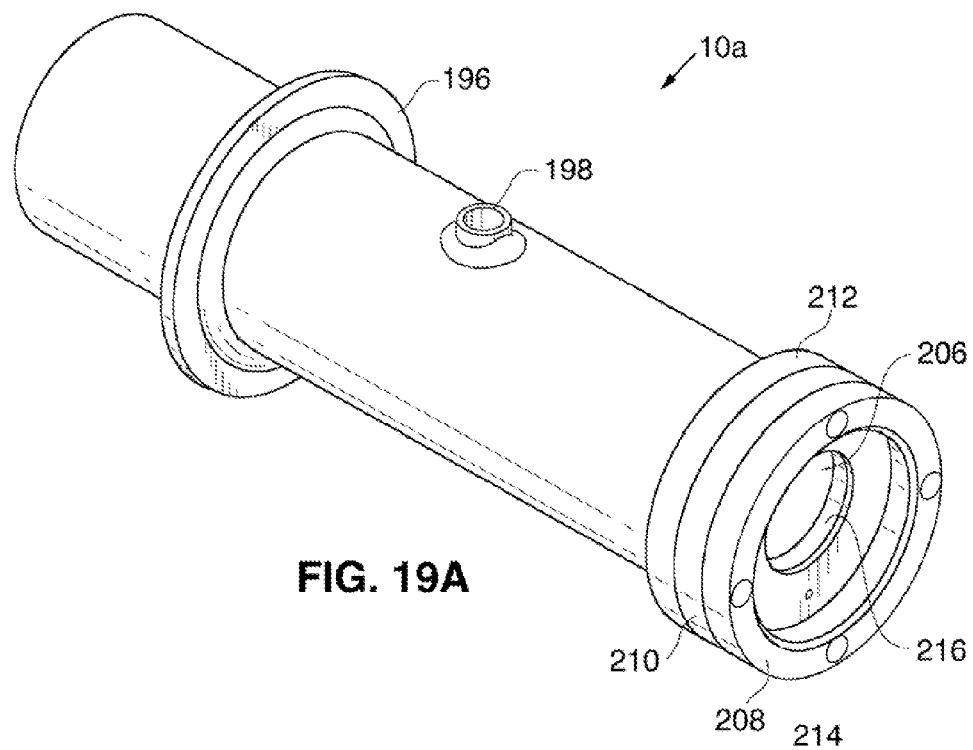
FIG. 19A is a perspective view of a second embodiment of an access cannula.
Figure 19B:
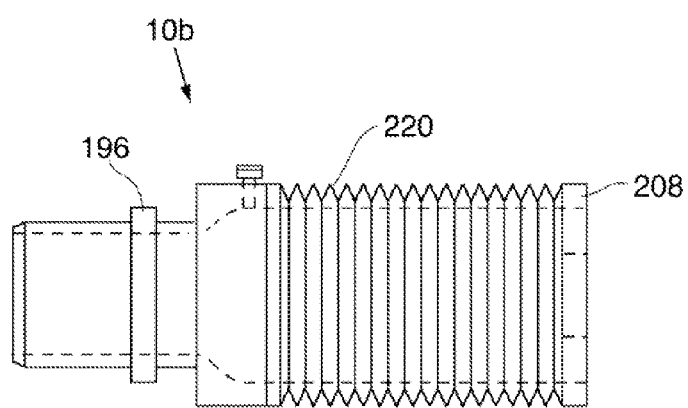
FIG. 19B is a side elevation view of a modification to the embodiment of FIG. 19A.

An alternative access cannula 10a shown in FIG. 19A includes a single lumen 206 and is provided without the fittings of the FIG. 18A/18B embodiment. In the FIG. 19A embodiment, a pair of proximal, middle, and distal annular plates 208, 210, 212 are coupled to the proximal end of the cannula 10a. A proximal seal 214 is anchored between the proximal plate 208 and the middle plate 210. A distal seal 216 is anchored between the middle plate 210 and the distal plate 212 such that the seals are spaced apart from another. The illustrated seals are annular seals each having an opening having a smaller diameter than the diameter of the overtube 12. In another variation shown in FIG. 19B, a portion of the access cannula 10b or its fittings (including one or all of the fittings of the FIG. 18A/18B embodiment) may include a longitudinally expandable bellows 220 proximal to face plate 209. Bellows 220 expand to accommodate the linkage prior to its deployment, but that can be compressed following deployment of the linkage to reduce the overall length of the access cannula 10.

The system 100 of FIG. 1A may be used for a variety of procedures to be carried out within the abdominal cavity, including resection, bypass, and/or anastomosis of the bowel, appendectomy, hysterectomy, ovary removal, cholecystectomy, prostatectomy and other procedures including those currently performed using laparoscopic or open surgical techniques. Use of the system 100 for surgery via umbilical access will next be described with reference to the system 100 of FIG. 1A and the access cannula 10a of FIG. 19A.

The system 100 is prepared for use by feeding the distal ends of the instruments 16 into the procedural cannulas 14, with the distal ends of the instruments preferably remaining within the lumens of the procedural cannulas 14. If a central tool cannula 14a is used, the central instrument is similarly fed through that cannula 14a, and an endoscope is preferably positioned to allow visualization at the distal end of the tool cannula. The linkage 26 (which has the procedural cannulas 14 coupled to it) is placed in the collapsed position.

An incision is formed through a desired location in the abdominal wall. The umbilicus or navel may be chosen as the location for the incision since it allows access through an existing scar and avoids the necessity for additional scars. The access cannula 10a is inserted into the incision. The collapsed linkage 26/procedural cannula 14 assembly is inserted into the access cannula 10a. The proximal and distal seals 214, 216 seal against the shaft of the overtube 12.

If the cannula 10 of FIGS. 18A/18B is instead used, the collapsed linkage 26/procedural cannula 14 assembly may be inserted into the proximal end fitting 200a of the access cannula 10, an endoscope is passed into fitting 200b, and any other instrument needed for the procedure is passed into the fitting 200c. The seals in the fittings 200a-c seal against the outer surfaces of the procedural cannulas 14, endoscope, etc.

Before the linkage 26/procedural cannula 14 assembly is advanced from the access cannula 10a into the abdominal cavity, insufflation gas is introduced into the cavity via insufflation port 198 (FIG. 19A) of the access cannula 19A. Once the cavity has been inflated, the linkage 26 is moved to the expanded position as described above (e.g. by advancing central retractor 14b or procedural cannula 14a (FIG. 4A) in a distal direction using the handle 18a of central tool/cannula 14a). Expansion of the linkage 26 orients the procedural cannulas 14 as shown in FIG. 2A The distal ends of the instruments 16 are advanced from the procedural cannulas 14, 14a and used to carry out the surgical procedure. The endoscope 20 may be advanced or oriented into a convenient position within the cavity. When reorientation of an instrument 16 is needed, the handle 18 of that instrument is manipulated, causing the associated control gimbal 126 to engage the pullwires associated with the procedural cannula 14 carrying that instrument. Once the procedure is completed, the instruments are withdrawn into the procedural cannulas 14, the linkage is collapsed (actively or by withdrawing it into the access cannula 10a). Any other instruments similarly withdrawn from the access cannula, the access cannula 10 is removed from the body, and the incision is closed in the usual fashion.

Figure 22:
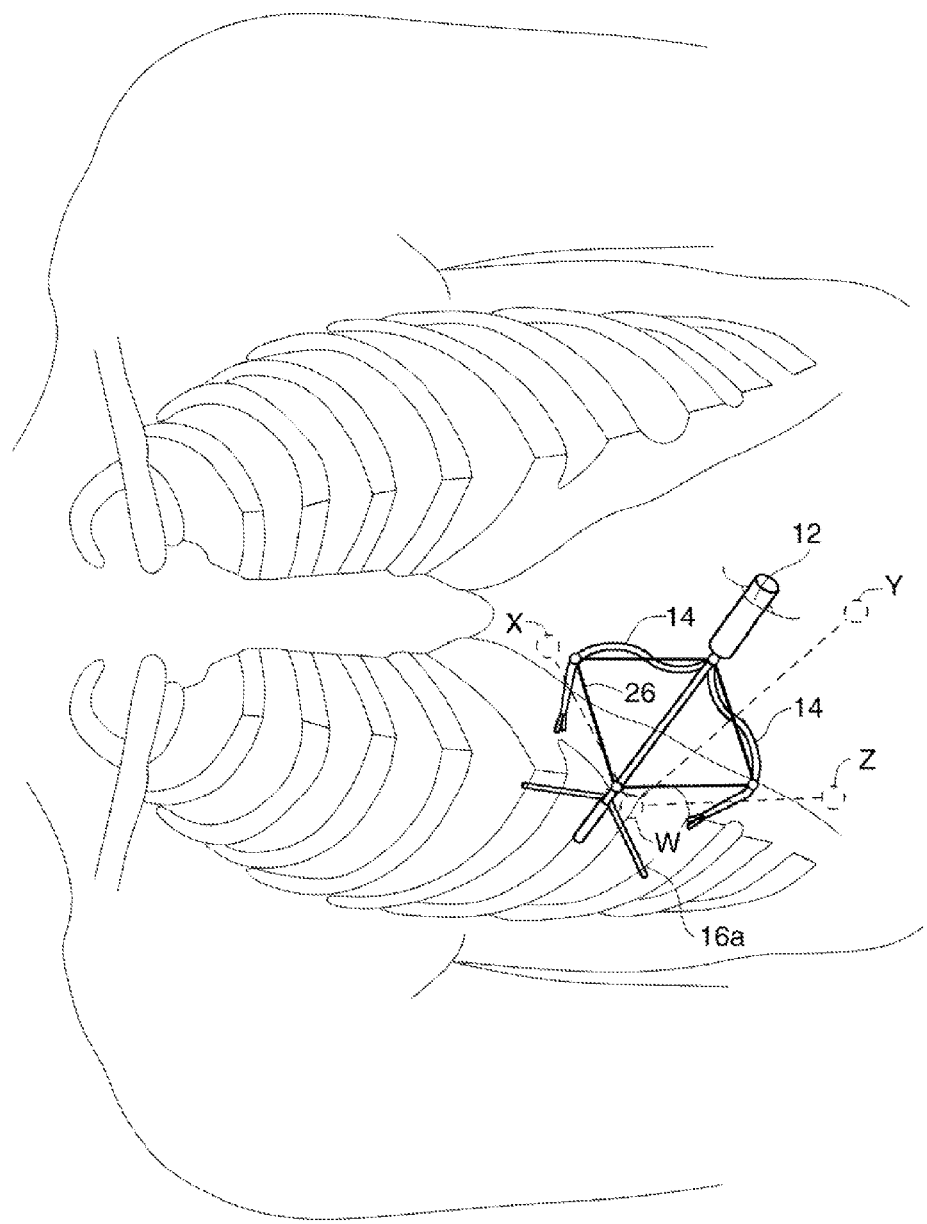
FIG. 22 schematically shows a patient lying prone on a surgical table and illustrates the system of FIG. 1A in use for surgery on a liver. The patient is shown as partially transparent to allow the system to be seen.

FIG. 22 schematically illustrates use of the disclosed system of FIG. 2 as used such as for a cholecystectomy procedure. According to such a procedure, the overtube 12 (with the procedural cannulas 14 extending through it) is introduced into the peritoneal space via a single abdominal port (not shown) and oriented towards the procedural site as shown. The overtube may be straight, but it will preferably have a bend tailored towards the quadrant of the abdominal cavity within which the procedure is to be carried out. Differently shaped overtubes may be used for different approaches (e.g. upper right quadrant vs. upper left quadrant approaches). The liver retractor 16c or retractor 16a (FIG. 2A) is used to lift and retract the liver superiorly away from the gallbladder and the operational area of the instruments 16. Instruments 16 are advanced through the procedural cannulas and used to perform the procedure. Whereas prior art laparoscopic procedures involve formation of three surgical ports or incisions labeled W (retractor port), X (right tool port), Y (scope port), Z (left tool port) in FIG. 22, use of the disclosed system allows the cholecystectomy procedure to be performed less invasively while allowing the surgeon to carry out the procedure from the same familiar perspective from which s/he would have performed the laparoscopic procedure. Using the linkage system, tools in the tool cannulas, the central retractor, and the scope are oriented to approach the operative site from the approximate directions that they would have taken if they had been advanced through ports X, Y, W and Z.

The illustrated embodiments utilize internal scaffold devices in single port procedures to locate tools at or near the abdominal walls such that the tools may be manipulated in a way that is intuitive to the surgeon given his/her experience with laparoscopic and/or open surgical techniques.

While certain embodiments have been described above, it should be understood that these embodiments are presented by way of example, and not limitation. It will be apparent to persons skilled in the relevant art that various changes in form and detail may be made therein without departing from the spirit and scope of the invention. This is especially true in light of technology and terms within the relevant art(s) that may be later developed.

Any and all patents, patent applications and printed publications referred to above are incorporated by reference.

We claim:

1. A method of performing a minimally invasive medical procedure within a body cavity, comprising the steps of:
   providing an access system including a mount, a rigid tube having a distal end and first and second cannulas extending from the distal end, and first and second actuators fixed to the mount;
   forming a percutaneous incision;
   advancing a distal end of the rigid tube through the incision to position the distal ends of the rigid tube and the cannulas within the body cavity;
   attaching the mount to an operating room fixture, the mount maintaining the position of the rigid tube in the incision;
   introducing a first end effector of a first instrument into a port on the first actuator, and advancing the end effector through the first cannula and out the distal end of the first cannula;
   introducing a second end effector of a second instrument into a port on the second actuator, and advancing the end effector through the second cannula and out the distal end of the second cannula;
   manipulating the handles of the first and second instruments, the handles engaging the actuator to deflect distal portions of the cannulas, said deflection altering the orientation of the instruments within the body cavity; and
   performing a procedure in the body cavity using the end effectors.

2. The method of claim 1, wherein engaging each actuator applies tension to pull cables extending between the actuator and the distal portion of the corresponding cannula.

3. The method of claim 2, wherein each second actuators comprises a gimbal having a distal member fixed to the mount and a proximal member connected to the pull cables and moveably coupled to the distal member, and wherein engaging the actuator moves the proximal member relative to the distal member.

4. The method of claim 3, wherein one of the distal and proximal members comprises a partially spherical socket and the other of the distal and proximal members comprises a partially spherical ball, and wherein engaging the actuator cause relative articulating of the partially spherical socket and the partially spherical ball.

5. The method of claim 1, further including introducing a distal end of a scope into a proximal opening on the mount, and advancing the scope distally, wherein advancing the scope distally advances the distal end of the scope through the rigid tube.

6. The method of claim 5, further including intruding a distal end of a third instrument into a proximal opening on the mount, and advancing the distal end of the third instrument distally, wherein advancing the third instrument distally advances the distal end of the third instrument through the rigid tube.

7. The method of claim 1, further including the step of locking the first or second actuator to retain the first or second cannula in a deflected position.

8. The method of claim 7, further including the step of, with the first or second cannula retained in the deflected position, withdrawing the tool from the retained cannula and inserting a different tool into the retained cannula.

9. The method of claim 1, further including:
positioning the distal portions of the first and second cannulas in a first, side by side, arrangement prior to advancing the rigid tube through the incision, and then increasing the lateral distance between the distal portions of the first and second cannulas after the advancing step.

10. The method of claim 1, wherein first and second handles are manipulated using the right and left hands of a single user.

11. The method of claim 1, wherein the system includes a third cannula within the rigid tube and having a distal end extending from the rigid tube, and wherein the method includes introducing a distal end of a third instrument into a proximal opening on the mount, and advancing the third instrument distally to advance the distal end into and through the third cannula.

12. The method of claim 1, wherein performing a procedure includes performing a procedure selected from the group consisting of appendectomy, hysterectomy, ovary removal, cholecystectomy, prostatectomy and resection, bypass, or anastomosis of the bowel.

13. The method of claim 1, further including:
introducing a distal end of a third instrument through the mount and the rigid tube and into the body cavity;
introducing a distal end of a fourth instrument through the mount and the rigid tube and into the body cavity;
and using the distal ends of the first, second, third and fourth instruments to carry out the procedure.

* * * * *